United States Patent
Hoss et al.

(10) Patent No.: US 9,636,450 B2
(45) Date of Patent: May 2, 2017

(54) PUMP SYSTEM MODULAR COMPONENTS FOR DELIVERING MEDICATION AND ANALYTE SENSING AT SEPERATE INSERTION SITES

(76) Inventors: Udo Hoss, Castro Valley, CA (US); Gary A. Stafford, Hayward, CA (US)

(*) Notice: Subject to any disclaimer, the term of this patent is extended or adjusted under 35 U.S.C. 154(b) by 731 days.

(21) Appl. No.: 12/032,593

(22) Filed: Feb. 15, 2008

(65) Prior Publication Data
US 2008/0200897 A1     Aug. 21, 2008

Related U.S. Application Data

(60) Provisional application No. 60/890,497, filed on Feb. 19, 2007.

(51) Int. Cl.
| A61M 5/142 | (2006.01) |
| A61M 5/36 | (2006.01) |
| A61M 5/172 | (2006.01) |
| A61M 5/145 | (2006.01) |

(52) U.S. Cl.
CPC ...... *A61M 5/14244* (2013.01); *A61M 5/1723* (2013.01); *A61M 5/1452* (2013.01); *A61M 5/365* (2013.01); *A61M 2005/14268* (2013.01); *A61M 2005/1726* (2013.01); *A61M 2205/3561* (2013.01); *A61M 2205/3592* (2013.01)

(58) Field of Classification Search
CPC ..... A61B 5/14865; A61B 5/415; A61B 5/418; A61B 5/6849; A61M 5/142; A61M 25/02
USPC ................... 604/66, 504; 600/345
See application file for complete search history.

(56) References Cited

U.S. PATENT DOCUMENTS

| 3,581,062 A | 5/1971 | Aston |
| 3,926,760 A | 12/1975 | Allen et al. |
| 3,949,388 A | 4/1976 | Fuller |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,425,920 A | 1/1984 | Bourland et al. |
| 4,441,968 A | 4/1984 | Emmer et al. |
| 4,464,170 A | 8/1984 | Clemens et al. |

(Continued)

FOREIGN PATENT DOCUMENTS

| CA | 2291105 | 12/1998 |
| DE | 4401400 | 7/1995 |

(Continued)

OTHER PUBLICATIONS

International Search Report and Written Opinion of the International Searching Authority for PCT Application No. PCT/US2008/054186 filed Feb. 16, 2008 to Abbott Diabetes Care, Inc. mailed Aug. 8, 2008.

(Continued)

*Primary Examiner* — Bhisma Mehta
*Assistant Examiner* — Matthew A Engel
(74) *Attorney, Agent, or Firm* — David Novak; Brannon Sowers & Cracraft PC

(57) ABSTRACT

Methods and systems for providing modular components in an integrated infusion device and analyte monitoring system where the components are independently replaceable are provided.

20 Claims, 11 Drawing Sheets

(56) References Cited

U.S. PATENT DOCUMENTS

| | | |
|---|---|---|
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,671,288 A | 6/1987 | Gough |
| 4,703,756 A | 11/1987 | Gough et al. |
| 4,711,245 A | 12/1987 | Higgins et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,145,381 A | 9/1992 | Volz |
| 5,165,407 A | 11/1992 | Wilson et al. |
| 5,193,545 A * | 3/1993 | Marsoner ............ A61B 5/14528 128/DIG. 13 |
| 5,202,261 A | 4/1993 | Musho et al. |
| 5,210,778 A | 5/1993 | Massart |
| 5,228,449 A | 7/1993 | Christ et al. |
| 5,231,988 A | 8/1993 | Wernicke et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,284,425 A | 2/1994 | Holtermann et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,715 A | 6/1994 | Berg |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,410,326 A | 4/1995 | Goldstein |
| 5,411,647 A | 5/1995 | Johnson et al. |
| 5,431,160 A | 7/1995 | Wilkins |
| 5,431,921 A | 7/1995 | Thombre |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,515,390 A | 5/1996 | Benton |
| 5,531,878 A | 7/1996 | Vadgama et al. |
| 5,543,326 A | 8/1996 | Heller et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,324 A | 5/1997 | Sarbach |
| 5,628,890 A | 5/1997 | Carter et al. |
| 5,653,239 A | 8/1997 | Pompei et al. |
| 5,660,163 A | 8/1997 | Schulman et al. |
| 5,665,222 A | 9/1997 | Heller et al. |
| 5,711,001 A | 1/1998 | Bussan et al. |
| 5,711,861 A | 1/1998 | Ward et al. |
| 5,735,285 A | 4/1998 | Albert et al. |
| 5,738,220 A * | 4/1998 | Geszler ................ A61N 1/056 206/365 |
| 5,772,586 A | 6/1998 | Heinonen et al. |
| 5,791,344 A | 8/1998 | Schulman et al. |
| 5,797,940 A | 8/1998 | Mawhirt et al. |
| 5,814,020 A * | 9/1998 | Gross ............... A61M 5/14248 604/141 |
| 5,820,551 A | 10/1998 | Hill et al. |
| 5,822,715 A | 10/1998 | Worthington et al. |
| 5,833,603 A | 11/1998 | Kovacs et al. |
| 5,842,189 A | 11/1998 | Keeler et al. |
| 5,858,001 A * | 1/1999 | Tsals ................ A61M 5/14248 604/135 |
| 5,899,855 A | 5/1999 | Brown |
| 5,918,603 A | 7/1999 | Brown |
| 5,925,021 A | 7/1999 | Castellano et al. |
| 5,931,814 A | 8/1999 | Gross et al. |
| 5,942,979 A | 8/1999 | Luppino |
| 5,951,521 A * | 9/1999 | Mastrototaro ..... A61B 5/14865 604/174 |
| 5,954,643 A | 9/1999 | Van Antwerp et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,980,708 A | 11/1999 | Champagne et al. |
| 5,993,411 A * | 11/1999 | Choi .................... A61M 5/158 600/347 |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,071,391 A | 6/2000 | Gotoh et al. |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,144,837 A | 11/2000 | Quy |

(56) References Cited

U.S. PATENT DOCUMENTS

| | | | |
|---|---|---|---|
| 6,159,147 | A | 12/2000 | Lichter et al. |
| 6,161,095 | A | 12/2000 | Brown |
| 6,162,611 | A | 12/2000 | Heller et al. |
| 6,175,752 | B1 | 1/2001 | Say et al. |
| 6,186,982 | B1 * | 2/2001 | Gross ............... A61M 5/14248 604/132 |
| 6,200,265 | B1 | 3/2001 | Walsh et al. |
| 6,212,416 | B1 | 4/2001 | Ward et al. |
| 6,219,574 | B1 | 4/2001 | Cormier et al. |
| 6,248,067 | B1 | 6/2001 | Causey, III et al. |
| 6,259,937 | B1 | 7/2001 | Schulman et al. |
| 6,270,455 | B1 | 8/2001 | Brown |
| 6,275,717 | B1 | 8/2001 | Gross et al. |
| 6,283,761 | B1 | 9/2001 | Joao |
| 6,284,478 | B1 | 9/2001 | Heller et al. |
| 6,293,925 | B1 | 9/2001 | Safabash et al. |
| 6,295,506 | B1 | 9/2001 | Heinonen et al. |
| 6,299,347 | B1 | 10/2001 | Pompei |
| 6,299,757 | B1 | 10/2001 | Feldman et al. |
| 6,306,104 | B1 | 10/2001 | Cunningham et al. |
| 6,309,884 | B1 | 10/2001 | Cooper et al. |
| 6,329,161 | B1 | 12/2001 | Heller et al. |
| 6,331,244 | B1 | 12/2001 | Lewis et al. |
| 6,338,790 | B1 | 1/2002 | Feldman et al. |
| 6,348,640 | B1 | 2/2002 | Navot et al. |
| 6,359,270 | B1 | 3/2002 | Bridson |
| 6,359,444 | B1 | 3/2002 | Grimes |
| 6,360,888 | B1 | 3/2002 | McIvor et al. |
| 6,366,794 | B1 | 4/2002 | Moussy et al. |
| 6,368,141 | B1 | 4/2002 | Van Antwerp et al. |
| 6,377,828 | B1 | 4/2002 | Chaiken et al. |
| 6,377,894 | B1 | 4/2002 | Deweese et al. |
| 6,379,301 | B1 | 4/2002 | Worthington et al. |
| 6,418,332 | B1 | 7/2002 | Mastrototaro et al. |
| 6,418,346 | B1 | 7/2002 | Nelson et al. |
| 6,424,847 | B1 | 7/2002 | Mastrototaro et al. |
| 6,427,088 | B1 | 7/2002 | Bowman, IV et al. |
| 6,440,068 | B1 | 8/2002 | Brown et al. |
| 6,445,374 | B2 | 9/2002 | Albert et al. |
| 6,458,109 | B1 * | 10/2002 | Henley ............... A61M 1/0088 604/289 |
| 6,461,496 | B1 | 10/2002 | Feldman et al. |
| 6,471,689 | B1 | 10/2002 | Joseph et al. |
| 6,478,736 | B1 | 11/2002 | Mault |
| 6,482,176 | B1 | 11/2002 | Wich |
| 6,484,046 | B1 | 11/2002 | Say et al. |
| 6,493,069 | B1 | 12/2002 | Nagashimada et al. |
| 6,497,655 | B1 | 12/2002 | Linberg et al. |
| 6,498,043 | B1 | 12/2002 | Schulman et al. |
| 6,503,381 | B1 | 1/2003 | Gotoh et al. |
| 6,512,939 | B1 | 1/2003 | Colvin et al. |
| 6,514,460 | B1 | 2/2003 | Fendrock |
| 6,514,689 | B2 | 2/2003 | Han et al. |
| 6,514,718 | B2 | 2/2003 | Heller et al. |
| 6,540,891 | B1 | 4/2003 | Stewart et al. |
| 6,546,268 | B1 | 4/2003 | Ishikawa et al. |
| 6,549,796 | B2 | 4/2003 | Sohrab |
| 6,551,494 | B1 | 4/2003 | Heller et al. |
| 6,554,795 | B2 | 4/2003 | Lam et al. |
| 6,558,320 | B1 | 5/2003 | Causey, III et al. |
| 6,558,321 | B1 | 5/2003 | Burd et al. |
| 6,560,471 | B1 | 5/2003 | Heller et al. |
| 6,561,978 | B1 | 5/2003 | Conn et al. |
| 6,562,001 | B2 | 5/2003 | Lebel et al. |
| 6,564,105 | B2 | 5/2003 | Starkweather et al. |
| 6,565,509 | B1 | 5/2003 | Say et al. |
| 6,571,128 | B2 | 5/2003 | Lebel et al. |
| 6,572,545 | B2 | 6/2003 | Knobbe et al. |
| 6,576,101 | B1 | 6/2003 | Heller et al. |
| 6,577,899 | B2 | 6/2003 | Lebel et al. |
| 6,579,690 | B1 | 6/2003 | Bonnecaze et al. |
| 6,585,644 | B2 | 7/2003 | Lebel et al. |
| 6,591,125 | B1 | 7/2003 | Buse et al. |
| 6,592,745 | B1 | 7/2003 | Feldman et al. |
| 6,595,919 | B2 | 7/2003 | Berner et al. |
| 6,600,997 | B2 | 7/2003 | Deweese et al. |
| 6,605,200 | B1 | 8/2003 | Mao et al. |
| 6,605,201 | B1 | 8/2003 | Mao et al. |
| 6,607,509 | B2 | 8/2003 | Bobroff et al. |
| 6,610,012 | B2 | 8/2003 | Mault |
| 6,616,819 | B1 | 9/2003 | Liamos et al. |
| 6,618,934 | B1 | 9/2003 | Feldman et al. |
| 6,633,772 | B2 | 10/2003 | Ford et al. |
| 6,635,014 | B2 | 10/2003 | Starkweather et al. |
| 6,641,533 | B2 | 11/2003 | Causey, III et al. |
| 6,648,821 | B2 | 11/2003 | Lebel et al. |
| 6,650,471 | B2 | 11/2003 | Doi |
| 6,654,625 | B1 | 11/2003 | Say et al. |
| 6,656,114 | B1 | 12/2003 | Poulsen et al. |
| 6,658,396 | B1 | 12/2003 | Tang et al. |
| 6,659,948 | B2 | 12/2003 | Lebel et al. |
| 6,668,196 | B1 | 12/2003 | Villegas et al. |
| 6,675,030 | B2 | 1/2004 | Ciuczak et al. |
| 6,676,816 | B2 | 1/2004 | Mao et al. |
| 6,687,546 | B2 | 2/2004 | Lebel et al. |
| 6,689,056 | B1 | 2/2004 | Kilcoyne et al. |
| 6,694,191 | B2 | 2/2004 | Starkweather et al. |
| 6,695,860 | B1 | 2/2004 | Ward et al. |
| 6,702,857 | B2 | 3/2004 | Brauker et al. |
| 6,730,200 | B1 | 5/2004 | Stewart et al. |
| 6,733,446 | B2 | 5/2004 | Lebel et al. |
| 6,736,957 | B1 | 5/2004 | Forrow et al. |
| 6,740,075 | B2 | 5/2004 | Lebel et al. |
| 6,740,518 | B1 | 5/2004 | Duong et al. |
| 6,741,877 | B1 | 5/2004 | Shults et al. |
| 6,746,582 | B2 | 6/2004 | Heller et al. |
| 6,749,740 | B2 | 6/2004 | Liamos et al. |
| 6,758,810 | B2 | 7/2004 | Lebel et al. |
| 6,758,835 | B2 * | 7/2004 | Close ............... A61B 5/153 600/327 |
| 6,764,581 | B1 | 7/2004 | Forrow et al. |
| 6,770,030 | B1 | 8/2004 | Schaupp et al. |
| 6,773,671 | B1 | 8/2004 | Lewis et al. |
| 6,789,195 | B1 | 9/2004 | Prihoda et al. |
| 6,790,178 | B1 | 9/2004 | Mault et al. |
| 6,804,558 | B2 | 10/2004 | Haller et al. |
| 6,809,653 | B1 | 10/2004 | Mann et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,813,519 | B2 | 11/2004 | Lebel et al. |
| 6,837,988 | B2 | 1/2005 | Leong et al. |
| 6,862,465 | B2 | 3/2005 | Shults et al. |
| 6,865,407 | B2 | 3/2005 | Kimball et al. |
| 6,873,268 | B2 | 3/2005 | Lebel et al. |
| 6,878,112 | B2 | 4/2005 | Linberg et al. |
| 6,881,551 | B2 | 4/2005 | Heller et al. |
| 6,882,940 | B2 | 4/2005 | Potts et al. |
| 6,892,085 | B2 | 5/2005 | McIvor et al. |
| 6,893,545 | B2 | 5/2005 | Gotoh et al. |
| 6,895,263 | B2 | 5/2005 | Shin et al. |
| 6,895,265 | B2 | 5/2005 | Silver |
| 6,923,763 | B1 | 8/2005 | Kovatchev et al. |
| 6,931,327 | B2 | 8/2005 | Goode, Jr. et al. |
| 6,932,892 | B2 | 8/2005 | Chen et al. |
| 6,932,894 | B2 | 8/2005 | Mao et al. |
| 6,936,006 | B2 | 8/2005 | Sabra |
| 6,942,518 | B2 | 9/2005 | Liamos et al. |
| 6,950,708 | B2 | 9/2005 | Bowman IV et al. |
| 6,958,705 | B2 | 10/2005 | Lebel et al. |
| 6,968,294 | B2 | 11/2005 | Gutta et al. |
| 6,971,274 | B2 | 12/2005 | Olin |
| 6,971,999 | B2 | 12/2005 | Py et al. |
| 6,974,437 | B2 | 12/2005 | Lebel et al. |
| 6,983,176 | B2 | 1/2006 | Gardner et al. |
| 6,990,366 | B2 | 1/2006 | Say et al. |
| 6,997,907 | B2 | 2/2006 | Safabash et al. |
| 6,998,247 | B2 | 2/2006 | Monfre et al. |
| 7,003,336 | B2 | 2/2006 | Holker et al. |
| 7,003,340 | B2 | 2/2006 | Say et al. |
| 7,003,341 | B2 | 2/2006 | Say et al. |
| 7,016,713 | B2 | 3/2006 | Gardner et al. |
| 7,024,245 | B2 | 4/2006 | Lebel et al. |
| 7,025,425 | B2 | 4/2006 | Kovatchev et al. |

(56) References Cited

U.S. PATENT DOCUMENTS

| | | | |
|---|---|---|---|
| 7,027,848 B2 | 4/2006 | Robinson et al. |
| 7,027,931 B1 | 4/2006 | Jones et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,073,246 B2 | 7/2006 | Bhullar et al. |
| 7,074,307 B2 | 7/2006 | Simpson et al. |
| 7,081,195 B2 | 7/2006 | Simpson et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,125,382 B2 | 10/2006 | Zhou et al. |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,167,818 B2 | 1/2007 | Brown |
| 7,171,274 B2 | 1/2007 | Starkweather et al. |
| 7,174,199 B2 | 2/2007 | Berner et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,291,497 B2 | 11/2007 | Holmes et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,386,937 B2 | 6/2008 | Bhullar et al. |
| 7,404,796 B2 | 7/2008 | Ginsberg |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,474,992 B2 | 1/2009 | Ariyur |
| 7,494,465 B2 | 2/2009 | Brister et al. |
| 7,497,827 B2 | 3/2009 | Brister et al. |
| 7,519,408 B2 | 4/2009 | Rasdal et al. |
| 7,565,197 B2 | 7/2009 | Haubrich et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,613,491 B2 | 11/2009 | Boock et al. |
| 7,615,007 B2 | 11/2009 | Shults et al. |
| 7,630,748 B2 | 12/2009 | Budiman |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,766,829 B2 | 8/2010 | Sloan et al. |
| 7,768,386 B2 | 8/2010 | Hayter et al. |
| 7,774,145 B2 | 8/2010 | Brauker et al. |
| 7,775,444 B2 | 8/2010 | DeRocco et al. |
| 7,778,680 B2 | 8/2010 | Goode, Jr. et al. |
| 7,778,795 B2 | 8/2010 | Fukushima et al. |
| 7,811,231 B2 | 10/2010 | Jin et al. |
| 7,813,809 B2 | 10/2010 | Strother et al. |
| 7,826,981 B2 | 11/2010 | Goode, Jr. et al. |
| 7,866,026 B1 | 1/2011 | Wang et al. |
| 7,882,611 B2 | 2/2011 | Shah et al. |
| 7,889,069 B2 | 2/2011 | Fifolt et al. |
| 7,899,545 B2 | 3/2011 | John |
| 7,905,833 B2 | 3/2011 | Brister et al. |
| 7,911,010 B2 | 3/2011 | Stetter |
| 7,914,450 B2 | 3/2011 | Goode, Jr. et al. |
| 7,920,906 B2 | 4/2011 | Goode et al. |
| 7,941,200 B2 | 5/2011 | Weinert et al. |
| 7,946,985 B2 | 5/2011 | Mastrototaro et al. |
| 7,954,385 B2 | 6/2011 | Raisanen |
| 7,972,296 B2 | 7/2011 | Braig et al. |
| 7,974,672 B2 | 7/2011 | Shults et al. |
| 7,976,466 B2 | 7/2011 | Ward et al. |
| 7,978,063 B2 | 7/2011 | Baldus et al. |
| 8,010,174 B2 | 8/2011 | Goode et al. |
| 8,192,394 B2 | 6/2012 | Estes et al. |
| 8,216,138 B1 | 7/2012 | McGarraugh et al. |
| 8,239,166 B2 | 8/2012 | Hayter et al. |
| 8,282,549 B2 | 10/2012 | Brauker et al. |
| 2001/0037366 A1 | 11/2001 | Webb et al. |
| 2002/0019022 A1 | 2/2002 | Dunn et al. |
| 2002/0019612 A1 | 2/2002 | Watanabe et al. |
| 2002/0042090 A1 | 4/2002 | Heller et al. |
| 2002/0050250 A1 | 5/2002 | Peterson et al. |
| 2002/0054320 A1 | 5/2002 | Ogino |
| 2002/0055711 A1 | 5/2002 | Lavi et al. |
| 2002/0068860 A1 | 6/2002 | Clark |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0147135 A1 | 10/2002 | Schnell |
| 2002/0161288 A1 | 10/2002 | Shin et al. |
| 2002/0169439 A1* | 11/2002 | Flaherty ............ A61M 5/14248 604/891.1 |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0055380 A1* | 3/2003 | Flaherty ............ A61M 5/14276 604/155 |
| 2003/0060692 A1 | 3/2003 | Ruchti et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0134347 A1 | 7/2003 | Heller et al. |
| 2003/0147515 A1 | 8/2003 | Kai et al. |
| 2003/0167035 A1 | 9/2003 | Flaherty et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199790 A1 | 10/2003 | Boecker et al. |
| 2003/0212379 A1 | 11/2003 | Bylund et al. |
| 2003/0217966 A1 | 11/2003 | Tapsak et al. |
| 2003/0225361 A1 | 12/2003 | Sabra |
| 2003/0236489 A1* | 12/2003 | Jacobson ............ A61M 5/16886 604/67 |
| 2004/0010186 A1 | 1/2004 | Kimball et al. |
| 2004/0010207 A1 | 1/2004 | Flaherty et al. |
| 2004/0011671 A1 | 1/2004 | Shults et al. |

(56) References Cited

U.S. PATENT DOCUMENTS

| | | |
|---|---|---|
| 2004/0015131 A1* | 1/2004 | Flaherty ............ A61M 5/14248 604/123 |
| 2004/0024553 A1 | 2/2004 | Monfre et al. |
| 2004/0034289 A1 | 2/2004 | Teller et al. |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0063435 A1 | 4/2004 | Sakamoto et al. |
| 2004/0064068 A1 | 4/2004 | DeNuzzio et al. |
| 2004/0064088 A1 | 4/2004 | Gorman et al. |
| 2004/0064096 A1 | 4/2004 | Flaherty et al. |
| 2004/0099529 A1 | 5/2004 | Mao et al. |
| 2004/0106858 A1 | 6/2004 | Say et al. |
| 2004/0116847 A1 | 6/2004 | Wall |
| 2004/0116866 A1 | 6/2004 | Gorman et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135684 A1 | 7/2004 | Steinthal et al. |
| 2004/0138588 A1 | 7/2004 | Saikley et al. |
| 2004/0147996 A1 | 7/2004 | Miazga et al. |
| 2004/0152622 A1 | 8/2004 | Keith et al. |
| 2004/0153032 A1 | 8/2004 | Garribotto et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0219664 A1 | 11/2004 | Heller et al. |
| 2004/0223985 A1 | 11/2004 | Dunfiled et al. |
| 2004/0225338 A1 | 11/2004 | Lebel et al. |
| 2004/0236200 A1 | 11/2004 | Say et al. |
| 2004/0249254 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0070777 A1 | 3/2005 | Cho et al. |
| 2005/0090607 A1 | 4/2005 | Tapsak et al. |
| 2005/0096516 A1 | 5/2005 | Soykan et al. |
| 2005/0103624 A1 | 5/2005 | Bhullar et al. |
| 2005/0112169 A1 | 5/2005 | Brauker et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0137530 A1 | 6/2005 | Campbell et al. |
| 2005/0143635 A1 | 6/2005 | Kamath et al. |
| 2005/0173245 A1 | 8/2005 | Feldman et al. |
| 2005/0176136 A1 | 8/2005 | Burd et al. |
| 2005/0182306 A1 | 8/2005 | Sloan |
| 2005/0182358 A1 | 8/2005 | Veit et al. |
| 2005/0187442 A1 | 8/2005 | Cho et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0211572 A1 | 9/2005 | Buck et al. |
| 2005/0214892 A1 | 9/2005 | Kovatchev et al. |
| 2005/0215871 A1 | 9/2005 | Feldman et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0251033 A1 | 11/2005 | Scarantino et al. |
| 2005/0272985 A1 | 12/2005 | Kotulla et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004603 A1 | 1/2006 | Peterka et al. |
| 2006/0009727 A1 | 1/2006 | O'Mahony et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0091006 A1 | 5/2006 | Wang et al. |
| 2006/0142651 A1 | 6/2006 | Brister et al. |
| 2006/0154642 A1 | 7/2006 | Scannell |
| 2006/0156796 A1 | 7/2006 | Burke et al. |
| 2006/0166629 A1 | 7/2006 | Reggiardo |
| 2006/0169599 A1 | 8/2006 | Feldman et al. |
| 2006/0173444 A1 | 8/2006 | Choy et al. |
| 2006/0173712 A1 | 8/2006 | Joubert |
| 2006/0181695 A1* | 8/2006 | Sage ................ A61M 5/14216 356/28.5 |
| 2006/0189863 A1 | 8/2006 | Heller et al. |
| 2006/0193375 A1 | 8/2006 | Lee |
| 2006/0202805 A1 | 9/2006 | Schulman et al. |
| 2006/0211072 A1 | 9/2006 | Ryan et al. |
| 2006/0222566 A1 | 10/2006 | Brauker et al. |
| 2006/0224141 A1 | 10/2006 | Rush et al. |
| 2006/0226985 A1 | 10/2006 | Goodnow et al. |
| 2006/0233839 A1 | 10/2006 | Jacquet |
| 2006/0247508 A1 | 11/2006 | Fennell |
| 2006/0247710 A1 | 11/2006 | Goetz et al. |
| 2006/0253085 A1* | 11/2006 | Geismar ............ A61B 5/14532 604/272 |
| 2006/0253086 A1* | 11/2006 | Moberg ............... A61M 5/1413 604/272 |
| 2006/0253296 A1 | 11/2006 | Liisberg et al. |
| 2006/0258929 A1 | 11/2006 | Goode et al. |
| 2006/0264926 A1* | 11/2006 | Kochamba ........ A61M 5/14248 606/41 |
| 2006/0281985 A1 | 12/2006 | Ward et al. |
| 2006/0287591 A1 | 12/2006 | Ocvirk et al. |
| 2006/0287691 A1 | 12/2006 | Drew |
| 2006/0290496 A1 | 12/2006 | Peeters et al. |

(56) References Cited

U.S. PATENT DOCUMENTS

| | | |
|---|---|---|
| 2006/0293576 A1 | 12/2006 | Van Antwerp et al. |
| 2006/0293577 A1 | 12/2006 | Morrison et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0027381 A1 | 2/2007 | Stafford |
| 2007/0032706 A1 | 2/2007 | Kamath et al. |
| 2007/0032717 A1 | 2/2007 | Brister et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066956 A1 | 3/2007 | Finkel |
| 2007/0068807 A1 | 3/2007 | Feldman et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078818 A1 | 4/2007 | Zvitz et al. |
| 2007/0083153 A1* | 4/2007 | Haar ............... A61M 5/14244 604/67 |
| 2007/0093786 A1 | 4/2007 | Goldsmith et al. |
| 2007/0094216 A1 | 4/2007 | Mathias et al. |
| 2007/0095661 A1 | 5/2007 | Wang et al. |
| 2007/0100222 A1 | 5/2007 | Mastrototaro et al. |
| 2007/0106135 A1 | 5/2007 | Sloan et al. |
| 2007/0108048 A1 | 5/2007 | Wang et al. |
| 2007/0118405 A1 | 5/2007 | Campbell et al. |
| 2007/0149875 A1 | 6/2007 | Ouyang et al. |
| 2007/0153705 A1 | 7/2007 | Rosar et al. |
| 2007/0156033 A1 | 7/2007 | Causey, III et al. |
| 2007/0156094 A1 | 7/2007 | Safabash et al. |
| 2007/0161880 A1 | 7/2007 | Say et al. |
| 2007/0163880 A1 | 7/2007 | Woo et al. |
| 2007/0173706 A1 | 7/2007 | Neinast et al. |
| 2007/0173710 A1 | 7/2007 | Petisce et al. |
| 2007/0191701 A1 | 8/2007 | Feldman et al. |
| 2007/0199818 A1 | 8/2007 | Petyt et al. |
| 2007/0203407 A1 | 8/2007 | Hoss et al. |
| 2007/0203966 A1 | 8/2007 | Brauker et al. |
| 2007/0208246 A1 | 9/2007 | Brauker et al. |
| 2007/0213657 A1 | 9/2007 | Jennewine et al. |
| 2007/0219496 A1 | 9/2007 | Kamen et al. |
| 2007/0227911 A1 | 10/2007 | Wang et al. |
| 2007/0228071 A1 | 10/2007 | Kamen et al. |
| 2007/0233013 A1 | 10/2007 | Schoenberg et al. |
| 2007/0235331 A1 | 10/2007 | Simpson et al. |
| 2007/0244379 A1 | 10/2007 | Boock et al. |
| 2007/0244383 A1 | 10/2007 | Talbot et al. |
| 2007/0249922 A1 | 10/2007 | Peyser et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0271285 A1 | 11/2007 | Eichorn et al. |
| 2007/0299617 A1 | 12/2007 | Willis |
| 2008/0004515 A1 | 1/2008 | Jennewine et al. |
| 2008/0009692 A1 | 1/2008 | Stafford |
| 2008/0017522 A1 | 1/2008 | Heller et al. |
| 2008/0021436 A1 | 1/2008 | Wolpert et al. |
| 2008/0021666 A1 | 1/2008 | Goode, Jr. et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0057484 A1 | 3/2008 | Miyata et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0060955 A1 | 3/2008 | Goodnow |
| 2008/0061961 A1 | 3/2008 | John |
| 2008/0064943 A1 | 3/2008 | Talbot et al. |
| 2008/0066305 A1 | 3/2008 | Wang et al. |
| 2008/0071156 A1 | 3/2008 | Brister et al. |
| 2008/0071328 A1 | 3/2008 | Haubrich et al. |
| 2008/0077048 A1 | 3/2008 | Escutia et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0102441 A1 | 5/2008 | Chen et al. |
| 2008/0108942 A1 | 5/2008 | Brister et al. |
| 2008/0119703 A1 | 5/2008 | Brister et al. |
| 2008/0119705 A1 | 5/2008 | Patel et al. |
| 2008/0139910 A1 | 6/2008 | Mastrototaro et al. |
| 2008/0148873 A1 | 6/2008 | Wang |
| 2008/0156662 A1 | 7/2008 | Wu et al. |
| 2008/0161664 A1 | 7/2008 | Mastrototaro et al. |
| 2008/0161666 A1 | 7/2008 | Feldman et al. |
| 2008/0177149 A1 | 7/2008 | Weinert et al. |
| 2008/0182537 A1 | 7/2008 | Manku et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194934 A1 | 8/2008 | Ray et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208026 A1 | 8/2008 | Noujaim et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0255438 A1 | 10/2008 | Saidara et al. |
| 2008/0262469 A1 | 10/2008 | Brister et al. |
| 2008/0267823 A1 | 10/2008 | Wang et al. |
| 2008/0269723 A1 | 10/2008 | Mastrototaro et al. |
| 2008/0275313 A1 | 11/2008 | Brister et al. |
| 2008/0287761 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0300572 A1 | 12/2008 | Rankers et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312844 A1 | 12/2008 | Hayter et al. |
| 2008/0314395 A1 | 12/2008 | Kovatchev et al. |
| 2008/0319279 A1 | 12/2008 | Ramsay et al. |
| 2008/0319295 A1 | 12/2008 | Bernstein et al. |
| 2009/0005665 A1 | 1/2009 | Hayter et al. |
| 2009/0005666 A1 | 1/2009 | Shin et al. |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0020502 A1 | 1/2009 | Bhullar et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |

(56) References Cited

U.S. PATENT DOCUMENTS

| | | |
|---|---|---|
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054748 A1 | 2/2009 | Feldman et al. |
| 2009/0062633 A1 | 3/2009 | Brauker et al. |
| 2009/0062635 A1 | 3/2009 | Brauker et al. |
| 2009/0069750 A1* | 3/2009 | Schraga ............ A61M 5/14248 604/167.02 |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088787 A1 | 4/2009 | Koike et al. |
| 2009/0099436 A1 | 4/2009 | Brister et al. |
| 2009/0102678 A1 | 4/2009 | Mazza et al. |
| 2009/0105636 A1 | 4/2009 | Hayter et al. |
| 2009/0112478 A1 | 4/2009 | Mueller, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163789 A1 | 6/2009 | Say et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0227855 A1 | 9/2009 | Hill et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0259118 A1 | 10/2009 | Feldman et al. |
| 2009/0275817 A1 | 11/2009 | Feldman et al. |
| 2009/0287073 A1 | 11/2009 | Boock et al. |
| 2009/0287074 A1 | 11/2009 | Shults et al. |
| 2009/0292188 A1 | 11/2009 | Hoss et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0113897 A1 | 5/2010 | Brenneman et al. |
| 2010/0119693 A1 | 5/2010 | Tapsak et al. |
| 2010/0121169 A1 | 5/2010 | Petisce et al. |
| 2010/0141656 A1 | 6/2010 | Krieftewirth |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174157 A1 | 7/2010 | Brister et al. |
| 2010/0185069 A1 | 7/2010 | Brister et al. |
| 2010/0191082 A1 | 7/2010 | Brister et al. |
| 2010/0217105 A1 | 8/2010 | Yodfat et al. |
| 2010/0230285 A1 | 9/2010 | Hoss et al. |
| 2010/0234710 A1 | 9/2010 | Budiman et al. |
| 2010/0262201 A1 | 10/2010 | He et al. |
| 2010/0274111 A1 | 10/2010 | Say et al. |
| 2010/0280441 A1 | 11/2010 | Wilinska et al. |
| 2010/0331642 A1 | 12/2010 | Bruce et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0040256 A1 | 2/2011 | Bobroff et al. |
| 2011/0077490 A1 | 3/2011 | Simpson et al. |
| 2011/0097090 A1 | 4/2011 | Cao |
| 2011/0148905 A1 | 6/2011 | Simmons et al. |
| 2011/0178461 A1 | 7/2011 | Chong et al. |
| 2011/0208027 A1 | 8/2011 | Wagner et al. |
| 2011/0257895 A1 | 10/2011 | Brauker et al. |
| 2011/0263958 A1 | 10/2011 | Brauker et al. |
| 2011/0320130 A1 | 12/2011 | Valdes et al. |
| 2012/0053562 A1* | 3/2012 | Haase ............... A61M 5/14216 604/506 |
| 2012/0078071 A1 | 3/2012 | Bohm et al. |
| 2012/0108934 A1 | 5/2012 | Valdes et al. |
| 2012/0173200 A1 | 7/2012 | Breton et al. |
| 2012/0190989 A1 | 7/2012 | Kaiser et al. |
| 2012/0226121 A1 | 9/2012 | Kamath et al. |

FOREIGN PATENT DOCUMENTS

| | | |
|---|---|---|
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 0987982 | 1/2007 |
| EP | 2327362 | 6/2011 |
| EP | 2335587 | 6/2011 |

(56) References Cited

FOREIGN PATENT DOCUMENTS

| WO | WO-94/20602 | 9/1994 |
|---|---|---|
| WO | WO-96/25089 | 8/1996 |
| WO | WO-96/35370 | 11/1996 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/39086 | 5/2002 |
| WO | WO-02/058537 | 8/2002 |
| WO | WO-03/006091 | 1/2003 |
| WO | WO-03/090509 | 4/2003 |
| WO | WO-03/053503 | 7/2003 |
| WO | WO-03/071930 | 9/2003 |
| WO | WO-03/076893 | 9/2003 |
| WO | WO-03/082091 | 10/2003 |
| WO | WO-03/085372 | 10/2003 |
| WO | WO-03/103763 | 12/2003 |
| WO | WO-2004/061420 | 7/2004 |
| WO | WO-2005/041766 | 5/2005 |
| WO | WO-2005/089103 | 9/2005 |
| WO | WO-2005/119238 | 12/2005 |
| WO | WO-2006/024671 | 3/2006 |
| WO | WO-2006/079114 | 7/2006 |
| WO | WO-2006/108809 | 10/2006 |
| WO | WO-2006/118947 | 11/2006 |
| WO | WO-2006/121921 | 11/2006 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/143943 | 11/2008 |
| WO | WO-2011/002815 | 1/2011 |

OTHER PUBLICATIONS

International Preliminary Report on Patentability and Written Opinion of the International Searching Authority for PCT Application No. PCT/US2008/054186 filed Feb. 16, 2008, mailed Aug. 27, 2009.
Armour, J. C., et al., "Application of Chronic Intravascular Blood Glucose Sensor in Dogs", *Diabetes*, vol. 39, 1990, pp. 1519-1526.
Bennion, N., et al., "Alternate Site Glucose Testing: A Crossover Design", *Diabetes Technology & Therapeutics*, vol. 4, No. 1, 2002, pp. 25-33.
Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.
Brooks, S. L., et al., "Development of an On-Line Glucose Sensor for Fermentation Monitoring", *Biosensors*, vol. 3, 1987/88, pp. 45-56.
Cass, A. E., et al., "Ferrocene-Medicated Enzyme Electrode for Amperometric Determination of Glucose", *Analytical Chemistry*, vol. 56, No. 4, 1984, 667-671.
Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.
Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.
Isermann, R., "Supervision, Fault-Detection and Fault-Diagnosis Methods—An Introduction", *Control Engineering Practice*, vol. 5, No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Johnson, P. C., "Peripheral Circulation", *John Wiley & Sons*, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", *Diabetes Care*, vol. 24, No. 7, 2001, pp. 1303-1304.
Kaplan, S. M., "Wiley Electrical and Electronics Engineering Dictionary", *IEEE Press*, 2004, pp. 141, 142, 548, 549.
Lortz, J., et al., "What is Bluetooth? We Explain the Newest Short-Range Connectivity Technology", *Smart Computing Learning Series, Wireless Computing*, vol. 8, Issue 5, 2002, pp. 72-74.
Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.
McGarraugh, G., et al., "Glucose Measurements Using Blood Extracted from the Forearm and the Finger", *TheraSense, Inc.*, 2001, 16 Pages.
McGarraugh, G., et al., "Physiological Influences on Off-Finger Glucose Testing", *Diabetes Technology & Therapeutics*, vol. 3, No. 3, 2001, pp. 367-376.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.
Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.

(56) References Cited

OTHER PUBLICATIONS

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sternberg, R., et al., "Study and Development of Multilayer Needle-Type Enzyme-Based Glucose Microsensors", *Biosensors*, vol. 4, 1988, pp. 27-40.
Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.
Velho, G., et al., "Strategies for Calibrating a Subcutaneous Glucose Sensor", *Biomedica Biochimica Acta*, vol. 48, 1989, pp. 957-964.
Wilson, G. S., et al., "Progress Toward the Development of an Implantable Sensor for Glucose", *Clinical Chemistry*, vol. 38, No. 9, 1992, pp. 1613-1617.
European Patent Application No. 08730066.1, Extended European Search Report mailed Oct. 5, 2012.
U.S. Appl. No. 12/826,662, Advisory Action mailed Sep. 12, 2012.
U.S. Appl. No. 12/826,662, Office Action mailed Jul. 2, 2012.
Chinese Patent Application No. 20088005388.7, Original Language and English Translation of Office Action mailed May 15, 2012.
Russian Patent Application No. 2009135048, Original Language and English Translation of Office Action mailed Dec. 20, 2011.
U.S. Appl. No. 12/826,662, Office Action mailed Dec. 22, 2011.
Jobst, G., et al., "Thin-Film Microbiosensors for Glucose-Lactate Monitoring", *Analytical Chemistry*, vol. 68, No. 18, 1996, pp. 3173-3179.
Chinese Patent Application No. 20088005388.7, Original Language and English Translation of Office Action mailed Jul. 25, 2011.
Bremer, T. M., et al., "Benchmark Data from the Literature for Evaluation of New Glucose Sensing Technologies", *Diabetes Technology & Therapeutics*, vol. 3, No. 3, 2001, pp. 409-418.
Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.
Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.
Mougiakakou, et al., "A Real Time Simulation Model of Glucose-Insulin Metabolism for Type 1 Diabetes Patients", *Proceedings of the 2005 IEEE*, 2005, pp. 298-301.
Panteleon, A. E., et al., "The Role of the Independent Variable to Glucose Sensor Calibration", *Diabetes Technology & Therapeutics*, vol. 5, No. 3, 2003, pp. 401-410.
Parker, R., et al., "Robust H∞ Glucose Control in Diabetes Using a Physiological Model", *AIChE Journal*, vol. 46, No. 12, 2000, pp. 2537-2549.
U.S. Appl. No. 12/826,662, Office Action mailed Nov. 4, 2013.
Kuure-Kinsey, M., et al., "A Dual-Rate Kalman Filter for Continuous Glucose Monitoring", Proceedings of the 28th IEEE, EMBS Annual International Conference, New York City, Aug. 30-Sep. 3, 2006, pp. 63-66.
Morbiducci, U., et al., "Improved Usability of the Minimal Model of Insulin Sensitivity Based on an Automated Approach and Genetic Algorithms for Parameter Estimation", Clinical Science, vol. 112, No. 4, Aug. 2007, pp. 257-263.
Mougiakakou, et al., "A Real Time Simulation Model of Glucose-Insulin Metabolism for Type 1 Diabetes Patients", Proceedings of the 2005 IEEE, Engineering in Medicine and Biology 27th Annual Conference, Shanghai, China, Sep. 1-4, 2005, pp. 298-301.

\* cited by examiner

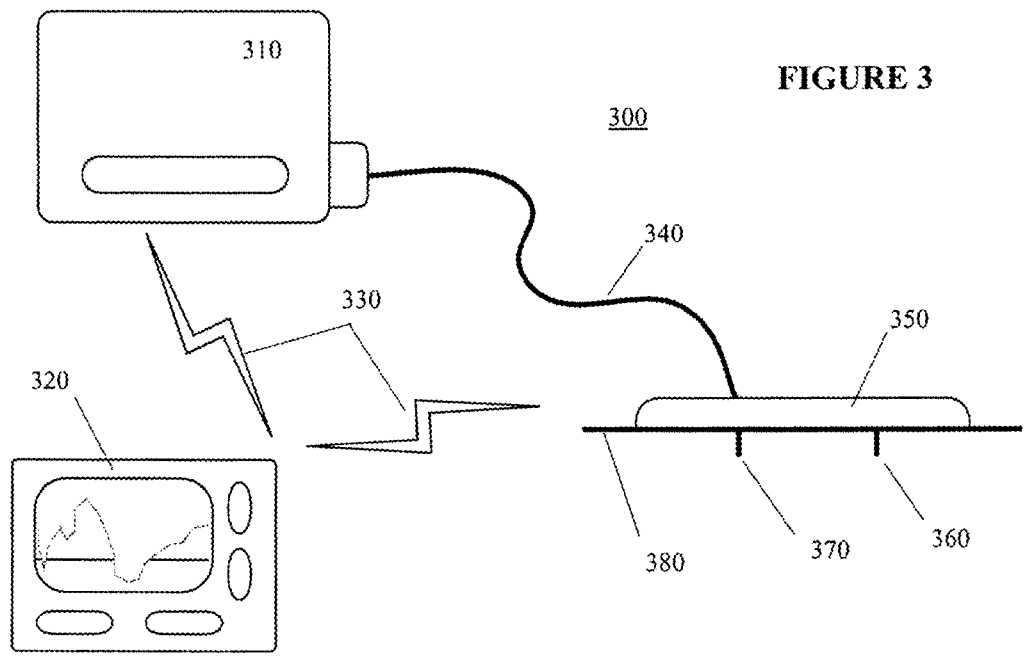
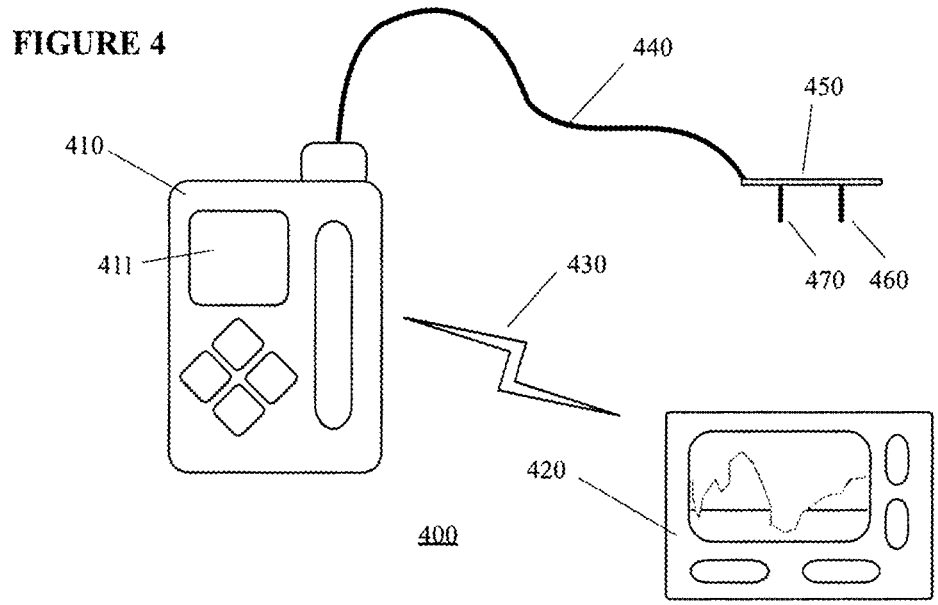

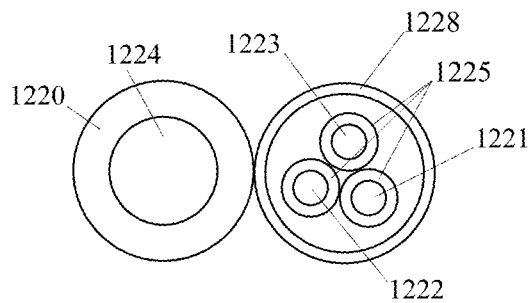
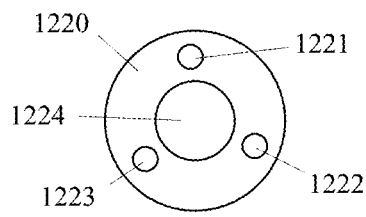
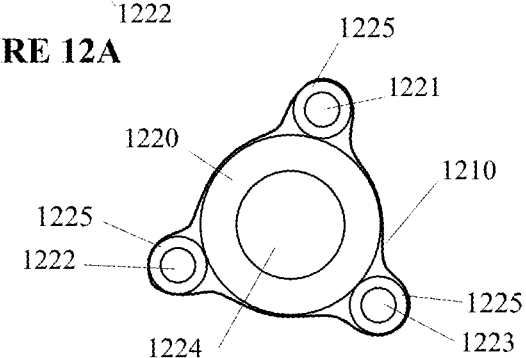
FIGURE 12A
FIGURE 12B
FIGURE 12C
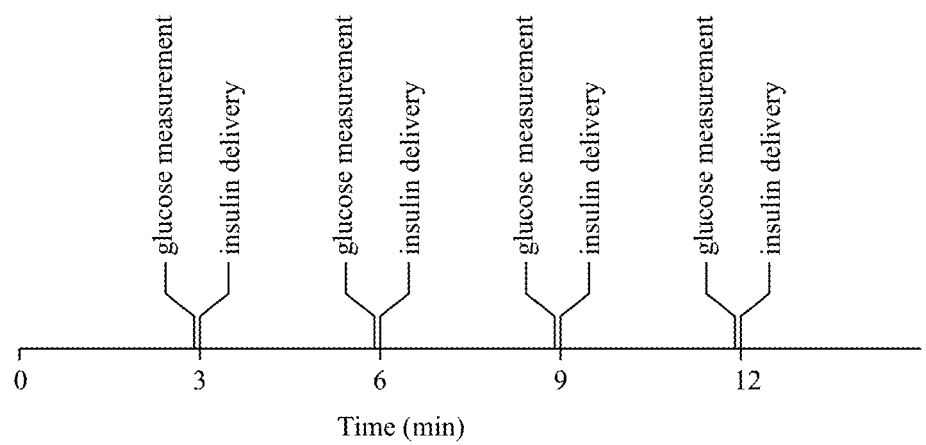
FIGURE 13

PUMP SYSTEM MODULAR COMPONENTS FOR DELIVERING MEDICATION AND ANALYTE SENSING AT SEPERATE INSERTION SITES

RELATED APPLICATION

The present application claims priority under §35 U.S.C. 119(e) to U.S. provisional patent application No. 60/890,497 filed Feb. 19, 2007, entitled "Modular Combination Of Medication Infusion And Analyte Monitoring", and assigned to the Assignee of the present application, Abbott Diabetes Care Inc. of Alameda, Calif., the disclosure of which is incorporated herein by reference for all purposes.

FIELD OF THE INVENTION

The present disclosure relates to methods and systems for integrating infusion systems and analyte monitoring systems. More specifically, the present disclosure relates to methods and systems for providing modular combination for integrated infusion and analyte monitoring systems.

BACKGROUND

Type 1 diabetics must periodically be administered with insulin to sustain their physiological conditions. Typically, these patients administer doses of either fast acting or slow acting insulin using needle type syringes, for example, prior to meals, and/or at a suitable time during the course of each day contemporaneously with the blood glucose level testing using fingerstick testing, for example. If insulin is not suitably administered, the diabetic patients risk serious if not fatal damage to the body.

Continued development and improvement in the external infusion pump therapy in recent years have drawn much appeal to the diabetic patients for, among others, improved management of diabetes by better regulating and controlling the intake of insulin. Typically, the patient inserts a cannula which is connected to as infusion tubing attached to an external pump, and insulin is administered based on a preprogrammed basal profiles. Moreover, the external infusion devices presently available include computational capability to determined suitable bolus doses such as carbohydrate bolus and correction bolus, for example, to be administered in conjunction with the infusion device executing the patient's basal profile.

The basal profiles are generally determined by the patient's physician or caretaker and are based on a number of factors including the patient's insulin sensitivity and physiological condition, which are diagnosed by the patient's physician, for example, and are typically intended to as accurately estimate the patient's glucose levels over a predetermined time period during which the patient is infusing insulin. The glucose levels may be estimated based on the patient's periodic discrete testing using a test strip and a blood glucose meter such as Freestyle® Glucose Meter available from Abbott Diabetes Care Inc., of Alameda, Calif. Such estimations are, however, prone to error, and do not accurately mirror the patient's actual physiological condition.

Furthermore, each aspect of the infusion and the analyte monitoring require components that are configured to execute the associated functions related to, for example, the control and management of insulin delivery and analyte monitoring. In addition, these components are prone to failure or otherwise periodic replacement due to ordinary usage. In view of the foregoing, it would be desirable to have a modular system including medication delivery unit such as an insulin pump, and an analyte monitoring device such as a continuous glucose monitoring system, that would allow for component based replacement when one or more aspects of the overall therapy management system fails or requires replacement.

SUMMARY

In accordance with the various embodiments of the present disclosure, there are provided method and system for modular combination of medication delivery and physiological condition monitoring.

These and other objects, features and advantages of the present disclosure will become more fully apparent from the following detailed description of the embodiments, the appended claims and the accompanying drawings.

BRIEF DESCRIPTION OF THE FIGURES

FIG. 3 illustrates an integrated infusion device and analyte monitoring system in accordance with yet another embodiment of the present disclosure;

FIG. 4 illustrates an integrated infusion device and analyte monitoring system in accordance with still another embodiment of the present disclosure;

FIG. 7A illustrates the integrated infusion device and monitoring system shown in FIG. 6 in further detail in one embodiment of the present disclosure, while

FIG. 11A illustrates a component perspective view of the infusion device cannula integrated with analyte monitoring system sensor electrodes in accordance with another embodiment of the present disclosure, while

FIGS. 12A-12C each illustrate a cross sectional view of the infusion device cannula integrated with continuous analyte monitoring system sensor electrodes of FIG. 10 in accordance with the various embodiments respectively, of the present disclosure;

FIG. 13 is a timing chart for illustrating the temporal spacing of blood glucose measurement and insulin delivery by the integrated infusion device and monitoring system in one embodiment;

DETAILED DESCRIPTION

Figure 1:
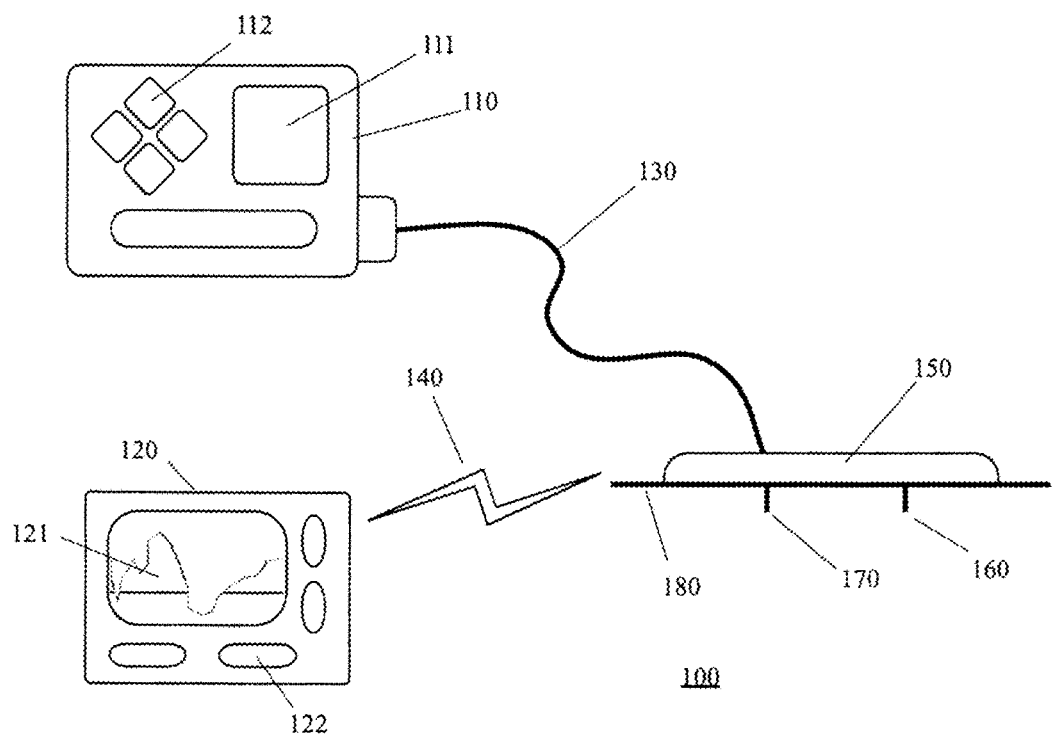
FIG. 1 illustrates an integrated infusion device and analyte monitoring system in accordance with one embodiment of the present disclosure.

FIG. 1 illustrates an integrated infusion device and analyte monitoring system in accordance with one embodiment of the present disclosure. Referring to FIG. 1, the integrated infusion device and analyte monitoring system 100 in one embodiment of the present disclosure includes an infusion device 110 connected to an infusion tubing 130 for liquid transport or infusion, and which is further coupled to a cannula 170. As can be seen from FIG. 1, the cannula 170 is configured to be mountably coupled to a transmitter unit 150, where the transmitter unit 150 is also mountably coupled to an analyte sensor 160. Also provided is an analyte monitor unit 120 which is configured to wirelessly communicate with the transmitter unit over a communication path 140.

Referring to FIG. 1, in one embodiment of the present disclosure, the transmitter unit 150 is configured for unidirectional wireless communication over the communication path 140 to the analyte monitor unit 120. In one embodiment, the analyte monitor unit 120 may be configured to include a transceiver unit (not shown) for bidirectional communication over the communication path 140. The transmitter unit 150 in one embodiment may be configured to periodically or continuously transmit signals associated with analyte levels detected by the analyte sensor 160 to the analyte monitor unit 120. The analyte monitor unit 120 may be configured to receive the signals from the transmitter unit 150 and in one embodiment, is configured to perform data storage and processing based on one or more preprogrammed or predetermined processes.

For example, in one embodiment, the analyte monitor unit 120 is configured to store the received signals associated with analyte levels in a data storage unit (not shown). Alternatively, or in addition, the analyte monitor unit 120 may be configured to process the signals associated with the analyte levels to generate trend indication by, for example, visual display of a line chart or an angular icon based display for output display on its display unit 121. Additional information may be output displayed on the display unit 121 of the analyte monitor unit 120 including, but not limited to, the substantially contemporaneous and monitored real time analyte level of the patient received from the transmitter unit 150 as detected by the sensor 160. The real time monitored analyte level may be displayed in a numeric format or in any other suitable format which provides the patient with the accurate measurement of the substantially real time analyte level detected by the sensor 160.

Analytes that may be monitored or determined by the sensor 160 include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Referring back to FIG. 1, the sensor 160 may include a short term (for example, 3 day, 5 day or 7 day use) analyte sensor which is replaced after its intended useful life. Moreover, in one embodiment, the sensor 160 is configured to be positioned subcutaneous to the skin of the patient such that at least a portion of the analyte sensor is maintained in fluid contact with the patient's analyte such as, for example, interstitial fluid or blood. In addition, the cannula 170 which is configured to similarly be positioned under the patient's skin is connected to the infusion tubing 130 of the infusion device 110 so as to deliver medication such as insulin to the patient. Moreover, in one embodiment, the cannula 170 is configured to be replaced with the replacement of the sensor 160.

In one aspect of the present disclosure, the cannula 170 and the sensor 160 may be configured to be subcutaneously positioned under the skin of the patient using an insertion mechanism (not shown) such as an insertion gun which may include, for example, a spring biased or loaded insertion mechanism to substantially accurately position the cannula 170 and the sensor 160 under the patient's skin. In this manner, the cannula 170 and the sensor 160 may be subcutaneously positioned with substantially little or no perceived pain by the patient. Alternatively, the cannula 170 and/or the sensor 160 may be configured to be manually inserted by the patient through the patient's skin. After positioning the cannula 170 and the sensor 160, they may be substantially firmly retained in position by an adhesive layer 180 which is configured to adhere to the skin of the patient for the duration of the time period during which the sensor 160 and the cannula 170 are subcutaneously positioned.

Moreover, in one embodiment, the transmitter unit 150 may be mounted after the subcutaneous positioning of the sensor 160 and the cannula 150 so as to be in electrical contact with the sensor electrodes. Similarly, the infusion tubing 130 may be configured to operatively couple to the housing of the transmitter unit 150 so as to be accurately positioned for alignment with the cannula 170 and to provide a substantially water tight seal. Exemplary analyte systems that may be employed are described in, for example, U.S. Pat. Nos. 6,134,461, 6,175,752, 6,121,611, 6,560,471, 6,746,582, and elsewhere.

Referring back to FIG. 1, the infusion device 110 may include capabilities to program basal profiles, calculation of bolus doses including, but not limited to, correction bolus, carbohydrate bolus, extended bolus, and dual bolus, which may be performed by the patient using the infusion device 110, and may be based on one or more factors including the patient's insulin sensitivity, insulin on board, intended carbohydrate intake (for example, for the carbohydrate bolus calculation prior to a meal), the patient's measured or detected glucose level, and the patient's glucose trend information. In a further embodiment, the bolus calculation capabilities may also be provided in the analyte monitor unit 120.

In one embodiment, the analyte monitor unit 120 is configured with a substantially compact housing that can be easily carried by the patient. In addition, the infusion device 110 similarly may be configured as a substantially compact device which can be easily and conveniently worn on the patient's clothing (for example, housed in a holster or a carrying device worn or clipped to the patient's belt or other parts of the clothing). Referring yet again to FIG. 1, the analyte monitor unit 120 and/or the infusion device 110 may include a user interface such as information input mechanism by the patient as well as data output including, for example, the display unit 121 on the analyte monitor unit 120, or similarly a display unit 111 on the infusion device 110.

One or more audio output devices such as, for example, speakers or buzzers may be integrated with the housing of the infusion device 110 and/or the analyte monitor unit 120 so as to output audible alerts or alarms based on the occurrence of one or more predetermined conditions associated with the infusion device 110 or the analyte monitor unit 120. For example, the infusion device 110 may be configured to output an audible alarm or alert to the patient upon detection of an occlusion in the infusion tubing 130 or the occurrence of a timed event such as a reminder to prime the infusion tubing upon replacement of the cannula 170, and the like.

The analyte monitor unit 120 may be similarly configured to output an audible alarm or alert when a predetermined condition or a pre-programmed event occurs, such as, for example, a reminder to replace the sensor 160 after its useful life (of, for example, 3 days, 5 days or 7 days, or more), or one or more alerts associated with the data received from the transmitter unit 150 corresponding to the patient's monitored analyte levels. Such alerts or alarms may include a warning alert to the patient that the detected analyte level is beyond a predetermined threshold level, or the trend of the detected analyte levels within a given time period is indicative of a significant condition such as potential hyperglycemia or hypoglycemia, which require attention or corrective action. It is to be noted that the examples of audible alarms and/or alerts are described above for illustrative purposes only, that within the scope of the present disclosure, other events or conditions may be programmed into the infusion device 110 or the analyte monitor unit 120 or both, so as to alert or notify the patient of the occurrence or the potential occurrence of such events or conditions.

In addition, within the scope of the present disclosure, audible alarms may be output alone, or in combination with one or more of a visual alert such as an output display on the display unit 111, 121 of the infusion device 110 or the analyte monitor unit 120, respectively, or vibratory alert which would provide a tactile indication to the patient of the associated alarm and/or alert.

Moreover, referring yet again to FIG. 1, while one analyte monitor unit 120 and one transmitter unit 150 are shown, within the scope of the present disclosure, additional analyte monitor units or transmitter units may be provided such that, for example, the transmitter unit 150 may be configured to transmit to multiple analyte monitor units substantially simultaneously. Alternatively, multiple transmitter units coupled to multiple sensors concurrently in fluid contact with the patient's analyte may be configured to transmit to the analyte monitor unit 120, or to multiple analyte monitor units. For example, an additional transmitter unit coupled to an additional sensor may be provided in the integrated infusion device and analyte monitoring system 100 which does not include the cannula 170, and which may be used to perform functions associated with the sensor 160 such as sensor calibration, sensor data verification, and the like.

In one embodiment, the transmitter unit 150 is configured to transmit the sampled data signals received from the sensor 160 without acknowledgement from the analyte monitor unit 120 that the transmitted sampled data signals have been received. For example, the transmitter unit 150 may be configured to transmit the encoded sampled data signals at a fixed rate (e.g., at one minute intervals, or any suitable rate) after the completion of the initial power on procedure. Likewise, the analyte monitor unit 120 may be configured to detect such transmitted encoded sampled data signals at predetermined time intervals. Alternatively, the transmitter unit 150 and the analyte monitor unit 120 may be configured for bi-directional communication over the communication path 140.

Additionally, in one aspect, the analyte monitor unit 120 may include two sections. The first section of the analyte monitor unit 120 may include an analog interface section that is configured to communicate with the transmitter unit 150 via the communication path 140. In one embodiment, the analog interface section may include an RF receiver and an antenna for receiving and amplifying the data signals from the transmitter unit 150, which are thereafter, demodulated with a local oscillator and filtered through a band-pass filter. The second section of the analyte monitor unit 120 may include a data processing section which is configured to process the data signals received from the transmitter unit 150 such as by performing data decoding, error detection and correction, data clock generation, and data bit recovery, for example.

In operation, upon completing the power-on procedure, the analyte monitor unit 120 is configured to detect the presence of the transmitter unit 150 within its range based on, for example, the strength of the detected data signals received from the transmitter unit 150 or predetermined transmitter identification information. Upon successful synchronization with the transmitter unit 150, the analyte monitor unit 120 is configured to begin receiving from the transmitter unit 150 data signals corresponding to the patient's detected analyte, for example glucose, levels.

Referring again to FIG. 1, the analyte monitor unit 120 or the infusion device 110, or both may be configured to further communicate with a data processing terminal (not shown) which may include a desktop computer terminal, a data communication enabled kiosk, a laptop computer, a handheld computing device such as a personal digital assistant (PDAs), or a data communication enabled mobile telephone, and the like, each of which may be configured for data communication via a wired or a wireless connection. The data processing terminal for example may include physician's terminal and/or a bedside terminal in a hospital environment.

The communication path 140 for data communication between the transmitter unit 150 and the analyte monitor unit 120 of FIG. 1 may include an RF communication link, Bluetooth® communication link, infrared communication link, or any other type of suitable wireless communication connection between two or more electronic devices. The data communication link may also include a wired cable connection such as, for example, but not limited to, an RS232 connection, USB connection, or serial cable connection.

Referring yet again to FIG. 1, in a further aspect of the present disclosure, the analyte monitor unit 120 or the infusion device 110 (or both) may also include a test strip port configured to receive a blood glucose test strip for discrete sampling of the patient's blood for glucose level determination. An example of the functionality of blood glucose test strip meter unit may be found in Freestyle® Blood Glucose Meter available from the assignee of the present disclosure, Abbott Diabetes Care Inc.

In the manner described above, in one embodiment of the present disclosure, the cannula 170 for infusing insulin or other suitable medication is integrated with the adhesive patch 180 for the sensor 160 and the transmitter unit 150 of the analyte monitoring system. Accordingly, only one on-skin patch can be worn by the patient (for example, on the skin of the abdomen) rather than two separate patches for the infusion device cannula 170, and the analyte monitoring system sensor 160 (with the transmitter unit 150). Thus, the Type-1 diabetic patient may conveniently implement infusion therapy in conjunction with real time glucose monitoring while minimizing potential skin irritation on the adhesive patch 180 site on the patient's skin, and thus provide more insertion sites with less irritation.

In addition, the integrated infusion device and analyte monitoring system 100 as shown in FIG. 1 may be configured such that the infusion tubing 130 may be disconnected from the infusion device 110 as well as from the housing of the transmitter unit 150 (or the adhesive patch 180) such that, optionally, the patient may configure the system as continuous analyte monitoring system while disabling the infusion device 110 functionality. Likewise, a patient may configure the system as an infusion device while disabling the continuous analyte monitoring system functions.

Moreover, in accordance with one embodiment of the present disclosure, the patient may better manage the physiological conditions associated with diabetes by having substantially continuous real time glucose data, trend information based on the substantially continuous real time glucose data, and accordingly, modify or adjust the infusion levels delivered by the infusion device 110 from the pre-programmed basal profiles that the infusion device 110 is configured to implement.

Figure 2:
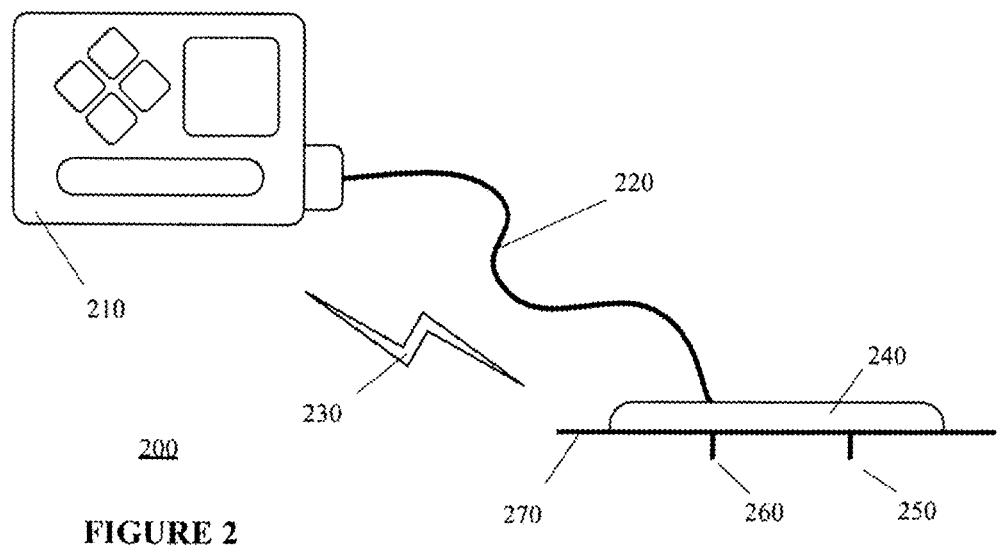
FIG. 2 illustrates an integrated infusion device and analyte monitoring system in accordance with another embodiment of the present disclosure.

FIG. 2 illustrates an integrated infusion device and analyte monitoring system in accordance with another embodiment of the present disclosure. Referring to FIG. 2, the integrated infusion device and analyte monitoring system 200 in one embodiment of the present disclosure includes an integrated infusion device and analyte monitor unit 210 which is coupled to an infusion tubing 220 connected to the cannula 260. Also shown in FIG. 2 is a transmitter unit 240 which is in electrical contact with an analyte sensor 250, where the cannula 260 and the analyte sensor 250 are subcutaneously positioned under the skin of the patient, and retained in position by an adhesive layer or patch 270.

Referring to FIG. 2, the integrated infusion device and analyte monitor unit 210 is configured to wirelessly communicate with the transmitter unit 240 over a communication path 230 such as an RF communication link. Compared with the embodiment shown in FIG. 1, it can be seen that in the embodiment shown in FIG. 2, the infusion device and the analyte monitor are integrated into a single housing 210. In this manner, the transmitter unit 240 may be configured to transmit signals corresponding to the detected analyte levels received from the analyte sensor 250 to the integrated infusion device and analyte monitor unit 210 for data analysis and processing.

Accordingly, the patient may conveniently receive real time glucose levels from the transmitter unit 240 and accordingly, determine whether to modify the existing basal profile (s) in accordance with which insulin is delivered to the patient. In this manner, the functionalities of the analyte monitor unit may be integrated within the compact housing of the infusion device to provide additional convenience to the patient, for example, by providing the real time glucose data as well as other relevant information such as glucose trend data to the user interface of the infusion device, so that the patient may readily and easily determine any suitable modification to the infusion rate of the insulin pump.

In one embodiment, the configurations of each component shown in FIG. 2 including the cannula 260, the analyte sensor 250, the transmitter unit 240, the adhesive layer 270, the communication path 230, as well as the infusion tubing 220 and the functionalities of the infusion device and the analyte monitor are substantially similar to the corresponding respective component as described above in conjunction with FIG. 1.

Accordingly, in one embodiment of the present disclosure, the additional convenience may be provided to the patient in maintaining and enhancing diabetes management by, for example, having a single integrated device such as the integrated infusion device and analyte monitor unit 210 which would allow the patient to easily manipulate and manage insulin therapy using a single user interface system of the integrated infusion device and analyte monitor unit 210. Indeed, by providing the information associated with both the glucose levels and insulin infusion in a single device, the patient may be provided with the additional convenience in managing diabetes and improving insulin therapy.

FIG. 3 illustrates an integrated infusion device and analyte monitoring system in accordance with yet another embodiment of the present disclosure. Referring to FIG. 3, the integrated infusion device and analyte monitoring system 300 in one embodiment of the present disclosure includes an infusion device 310 connected to an infusion tubing 340 coupled to a cannula 370. The cannula 370 is configured to be positioned subcutaneously under the patient's skin and substantially retained in position by an adhesive layer 380. Also retained in position, as discussed above and similar to the embodiments described in conjunction with FIGS. 1-2, is an analyte sensor 360 also positioned subcutaneously under the patient's skin and maintained in fluid contact with the patient's analyte. A transmitter unit 350 is provided so as to be electrically coupled to the analyte sensor 360 electrodes. Also, as can be seen from FIG. 3, in one embodiment, the infusion tubing 340 is connected to the housing of the transmitter unit 350 so as to connect to the cannula 370 disposed under the patient's skin.

Referring to FIG. 3, also provided is an analyte monitor unit 320 configured to wirelessly communicate with the transmitter unit 350 to receive data therefrom associated with the analyte levels of the patient detected by the analyte sensor 360. Referring to FIG. 3, in one embodiment, the infusion device 310 does not include a user interface such as a display unit and/or an input unit such as buttons or a jog dial. Instead, the user interface and control mechanism is provided on the analyte monitoring unit 320 such that the analyte monitoring unit 320 is configured to wirelessly control the operation of the infusion device 310 and further, to suitably program the infusion device 310 to execute pre-programmed basal profile(s), and to otherwise control the functionality of the infusion device 310.

More specifically, all of the programming and control mechanism for the infusion device 310 is provided in the analyte monitoring unit 320 such that when the patient is wearing the infusion device 310, it may be worn discreetly under clothing near the infusion site on the patient's skin (such as abdomen), while still providing convenient access to the patient for controlling the infusion device 310 through the analyte monitoring unit 320.

In addition, in one embodiment, the configurations of each component shown in FIG. 3 including the cannula 370, the analyte sensor 360, the transmitter unit 350, the adhesive layer 380, the communication path 330, as well as the infusion tubing 340 and the functionalities of the infusion device and the analyte monitoring unit 320 are substantially similar to the corresponding respective component as described above in conjunction with FIG. 1. However, the infusion device 310 in the embodiment shown in FIG. 3 is configured with a transceiver or an equivalent communication mechanism to communicate with the analyte monitoring unit 320.

In this manner, in one embodiment of the present disclosure, configuration of the infusion device 310 without a user interface provides a smaller and lighter housing and configuration for the infusion device 310 which would enhance the comfort in wearing and/or carrying the infusion device 310 with the patient. Moreover, since the control and programming functions of the infusion device 310 is provided on the analyte monitoring unit 320, the patient may conveniently program and/or control the functions and operations of the infusion device 310 without being tethered to the infusion tubing 340 attached to the cannula 370, which is positioned under the patient's skin. In addition, since the programming and control of the infusion device 310 is remotely performed on the analyte monitoring unit 320, the infusion tubing 340 may be shorter and thus less cumbersome.

FIG. 4 illustrates an integrated infusion device and analyte monitoring system in accordance with still another embodiment of the present disclosure. Referring to FIG. 4, the integrated infusion device and analyte monitoring system 400 in one embodiment of the present disclosure includes an infusion device 410 configured to wirelessly communicate with an analyte monitoring unit 420 over a communication path 430 such as an RF (radio frequency) link. In addition, as can be further seen from FIG. 4, the infusion device 410 is connected to an infusion tubing 440 which has provided therein integral wires connected to the analyte sensor electrodes. As discussed in further detail below, the measured analyte levels of the patient is received by the infusion device 410 via the infusion tubing 440 and transmitted to the analyte monitoring unit 420 for further processing and analysis.

More specifically, referring to FIG. 4, the integrated infusion device and analyte monitoring system 400 includes a patch 450 provided with a cannula 470 and an analyte sensor 460. The cannula 470 is configured to deliver or infuse medication such as insulin from the infusion device 410 to the patient. That is, in one embodiment, the cannula 470 and the analyte sensor 460 are configured to be positioned subcutaneous to the patient's skin. The analyte sensor 460 is configured to be positioned to be in fluid contact with the patient's analyte.

In this manner, the analyte sensor 460 is electrically coupled to integral wires provided within the infusion tubing 440 so as to provide signals corresponding to the measured or detected analyte levels of the patient to the infusion device 410. In one embodiment, the infusion device 410 is configured to perform data analysis and storage, such that the infusion device 410 may be configured to display the real time measured glucose levels to the patient on its display unit 411. In addition to or alternatively, the infusion device 410 is configured to wirelessly transmit the received signals from the analyte sensor 460 to the analyte monitoring unit 420 for data analysis, display, and/or storage and the analyte monitoring unit 420 may be configured to remotely control the functions and features of the infusion device 410 providing additional user convenience and discreteness.

Referring back to FIG. 4, in one embodiment, the patch 450 may be configured to be substantially small without a transmitter unit mounted thereon, and provided with a relatively small surface area to be attached to the patient's skin. In this manner, the patient may be provided with added comfort in having a substantially compact housing mounted on the skin (attached with an adhesive layer, for example), to infuse medication such as insulin, and for continuous analyte monitoring with the analyte sensor 460.

Figure 5:
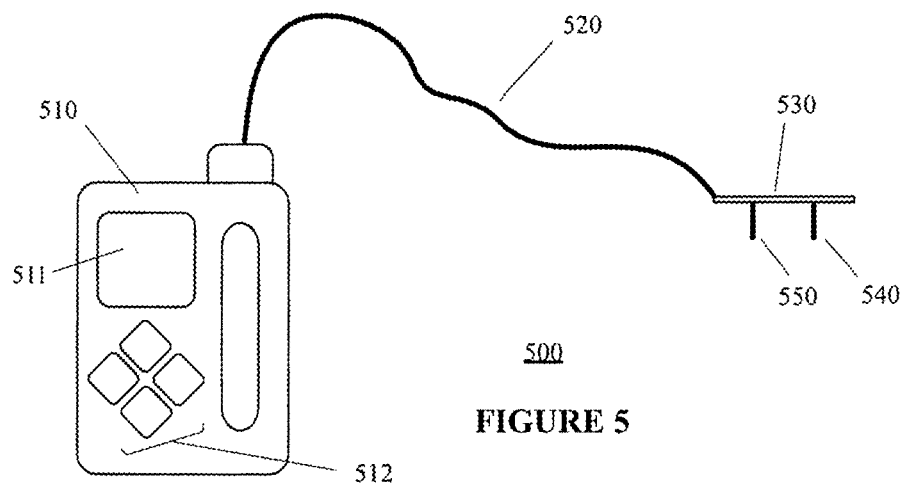
FIG. 5 illustrates an integrated infusion device and analyte monitoring system in accordance with still a further embodiment of the present disclosure.

FIG. 5 illustrates an integrated infusion device and analyte monitoring system in accordance with still a further embodiment of the present disclosure. As compared with the embodiment shown in FIG. 4, the integrated infusion device and analyte monitoring system 500 of FIG. 5 includes an integrated infusion device and analyte monitoring unit 510. Accordingly, one user interface is provided to the user including the display unit 511 and input buttons 512 provided on the housing of the integrated infusion device and analyte monitoring unit 510. Also shown in FIG. 5 are infusion tubing 520 with integral wires disposed therein and connected to analyte sensor 540 electrodes in fluid contact with the patient's analyte. Moreover, as can be seen from FIG. 5, an adhesive patch 530 is provided to retain the subcutaneous position of a cannula 550 and the analyte sensor 540 in the desired positions under the patient's skin.

Optionally, the integrated infusion device and analyte monitoring unit 510 may be provided with wireless or wired communication capability to communicate with a remote terminal such as a physician's computer terminal over a wireless communication path such as an RF communication link, or over a cable connection such as a USB connection, for example. Referring back to FIG. 5, in one embodiment of the present disclosure, the diabetic patient using an infusion therapy is provided with fewer components to handle or manipulate further simplifying insulin therapy and glucose level monitoring and management.

Figure 6:
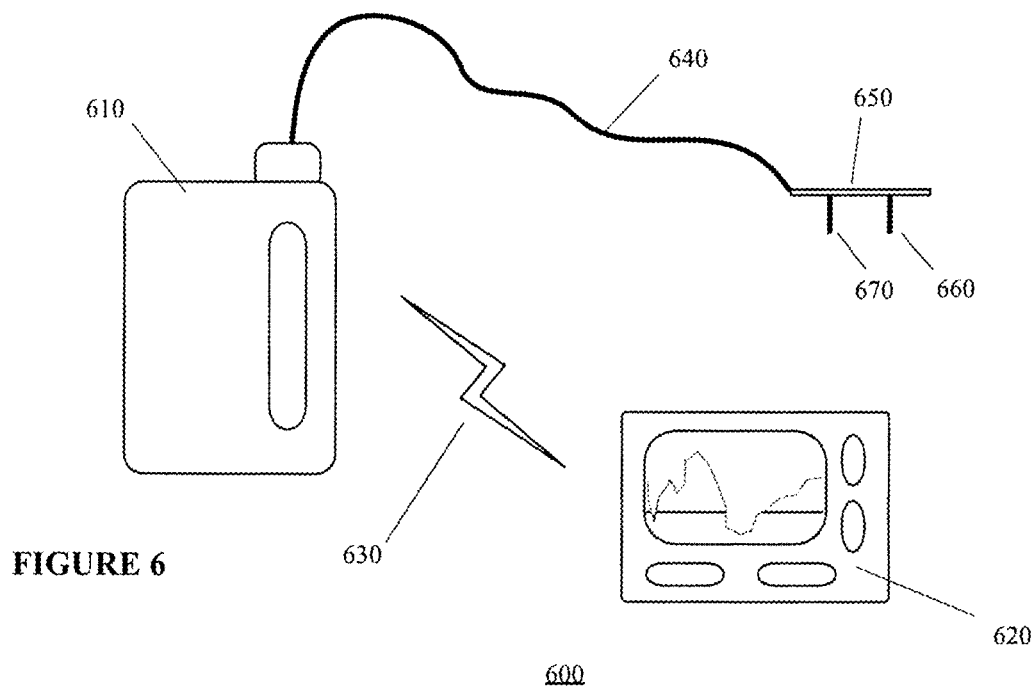
FIG. 6 illustrates an integrated infusion device and monitoring system in accordance with yet still a further embodiment of the present disclosure.

FIG. 6 illustrates an integrated infusion device and monitoring system in accordance with yet still a further embodiment of the present disclosure. Referring to FIG. 6, the integrated infusion device and analyte monitoring system 600 is provided with an infusion device without a user interface, and configured to wirelessly communicate with an analyte monitoring unit 620 over a communication path 630 such as an RF link. The infusion device 610, which may be provided in a compact housing since it does not incorporate the components associated with a user interface, is connected to an infusion tubing 640 having disposed therein integral wires correspondingly connected to the electrodes of analyte sensor 660 in fluid contact with the patient's analyte. In addition, the compact adhesive patch 650 in one embodiment is configured to retain cannula 670 and the analyte sensor 660 in the desired position under the skin of the patient.

Similar to the embodiment shown in FIG. 3, the analyte monitoring unit 620 is configured to control and program the infusion device 610 over the communication link 630. In this manner, the control and programming functions of the infusion device 610 may be remotely performed by the analyte monitoring unit 620, providing convenience to the patient.

Figure 7A:
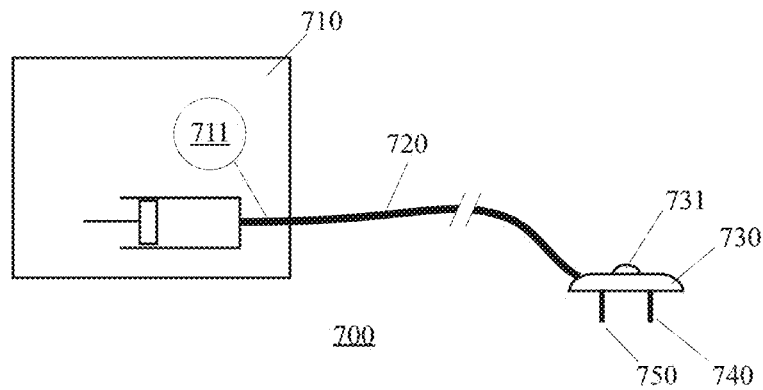
Figure 7B:
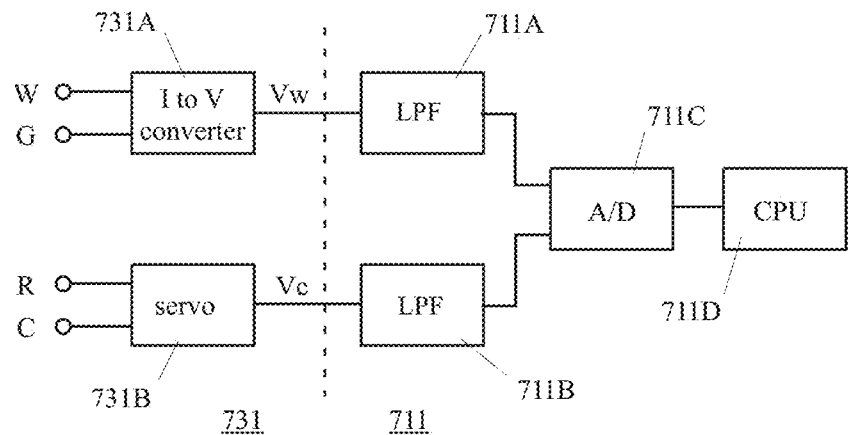
FIGS. 7B-7C illustrate the analog front end circuitry located at the patient interface and the pump assembly, respectively, of the integrated infusion device and monitoring system shown in FIG. 7A in accordance with one embodiment of the present disclosure.
Figure 7C:
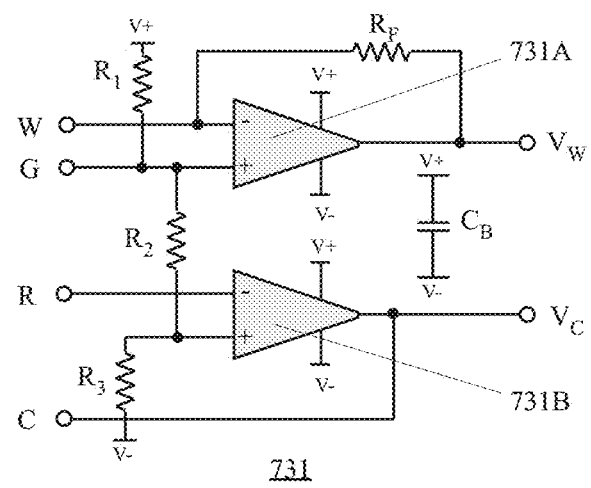

FIG. 7A illustrates the integrated infusion device and monitoring system shown in FIG. 6 in further detail in one embodiment of the present disclosure, while FIGS. 7B-7C illustrate the analog front end circuitry located at the patient interface and the pump assembly, respectively, of the integrated infusion device and monitoring system shown in FIG. 7A in accordance with one embodiment of the present disclosure. Referring to FIG. 7A, an infusion device 710 connected to an infusion tubing 720 with integral wires provided therein for connection to the electrodes of the analyte sensor is shown. The infusion tubing 720 is further connected to an adhesive patch 730 which is configured to retain cannula 750 and analyte sensor 740 in the desired subcutaneous position under the skin of the patient.

Referring to FIG. 7A, in one embodiment of the present disclosure, the infusion device 710 may be provided with a first analog front end circuitry unit 711, while the adhesive patch may be provided with a second analog front end circuitry unit 731. The integral wires from the analyte sensor 740 are configured to extend from the infusion device 710 to the adhesive patch 730 via the infusion tubing 720. Since the analyte sensor 740 in one embodiment is a passive component, the signals on the working electrode and the reference electrodes of the analyte sensors are subject to noise given the high impendence of the electrodes and the length of the integral wires (in excess of a few centimeters). The noise in turn may potentially adversely affect the signals on the working and reference electrodes, which may distort the measured analyte levels detected by the analyte sensor 740.

Given the length of the integral wire which corresponds to the length of the infusion tubing 720, in one embodiment, the signals from the working and reference electrodes may be converted to low impedance signals to minimize adverse impact from the noise. Accordingly, the infusion device 710 may be provided with a first analog front end circuitry unit 711, while the adhesive patch 730 may be provided with a second analog front end circuitry unit 731 as discussed in further detail below in conjunction with FIGS. 7B and 7C.

Referring now to FIG. 7B, the second analog front end circuitry unit 731 disposed on the adhesive patch 730 on the patient's skin, in one embodiment includes a trans-impedance amplifier (current to voltage converter or "I-to-V") 731A configured to convert the working electrode (W) current to a voltage (Vw), and to provide a guard signal (G), and a servo segment 731B to drive the counter electrode (C) voltage (Vc) based on the reference electrode (R) voltage. Also shown in FIG. 7B is a Low-Pass Filter (LPF) and gain stage 711A that follow each of the I-to-V and servo stages, and which is configured in one embodiment to drive an A/D (Analog-to-Digital) converter unit 711C whose results are read by a controller such as a central processing unit (CPU) 711D. The A/D converter unit 711C and the CPU 711D and other peripherals may be combined into a single integrated circuit (IC) known as a microcontroller (μC) such as the MSP430 product line.

Referring now to FIG. 7C, in one embodiment, the second analog front end circuitry unit 731 may be implemented by a pair of operational amplifiers (731A and 731B), four resistors (R1, R2, R3, $R_F$), and a bypass capacitor (Cb). The I-to-F stage using operational amplifier 731A is generated by the action of the input current from the working electrode (W) flowing through the feedback resistor ($R_F$) and creating a voltage differential that is driven by the operational amplifier 731A as the low impedance signal Vw. The offset for the Vw signal is established by the resistor divider comprised of R1, R2 and R3, which also creates the voltage of the guard signal (G)—a signal that is at the same potential or voltage as the working electrode (W).

The servo, using operational amplifier 731B, in one embodiment, drives the counter electrode (C) voltage to the sensor so that the reference electrode (R) is at the second value set by the resistor divider comprised of resistors R1, R2 and R3. This maintains the working electrode (W) voltage above the reference electrode (R) by a set amount known as the "Poise Voltage" (i.e 40 mV). The bypass capacitor (Cb) may be a small, low equivalent series resistance (ESR) capacitor, such as a 0.1 uF (100 nF) multi-layer ceramic (MLC) capacitor, that acts to provide local energy and reduce noise on the circuit. The voltage source for this circuit may be provided by the potential difference between V+ and V− where, for example, V+ may be 5V and V− may be ground (GND) or V+ may be +3V and V− may be −3V.

In one embodiment, the operational amplifiers 731A, 731B may be acquired as a dual operational amplifier integrated circuit (IC) in a single, small 8-pin, surface mount technology (SMT) package such as the OPA2349 in a SOT23-8 package (3 mm by 3 mm). Similar dual operational amplifier products may be available in even smaller ball-grid array (BGA) packages and as bare die that may be mounted directly to the circuit substrate, such as a printed circuit board (PCB) or flex circuit, using techniques such as "flip-chip" and wire-bond.

In one aspect, the analyte sensor described above in conjunction with the Figures may include one or more working electrodes and a reference electrode or a reference/counter electrode disposed on a substrate, and further, may optionally include a separate counter electrode. Indeed, in one aspect, the various electrodes of the sensor as well as the substrate and the dielectric layers may be provided in a stacked, side by side, or layered configuration or construction. For example, in one aspect, the sensor may include a substrate layer and a first conducting layer such as a carbon trace disposed on at least a portion of the substrate layer, and which may comprise the working electrode. Also shown disposed on at least a portion of the first conducting layer is a sensing layer.

A first insulation layer such as a first dielectric layer may be disposed or stacked on at least a portion of the first conducting layer, and further, a second conducting layer such as another carbon trace may be disposed or stacked on top of at least a portion of the first insulation layer (or dielectric layer). The second conducting layer may comprise the reference electrode, and in one aspect, may include a layer of silver/silver chloride (Ag/AgCl).

Further, a second insulation layer such as a dielectric layer in one embodiment may be disposed or stacked on at least a portion of the second conducting layer. Further, a third conducting layer, which may include carbon trace and that may comprise the counter electrode, may be disposed on at least a portion of the second insulation layer. Finally, a third insulation layer may be disposed or stacked on at least a portion of the third conducting layer. In this manner, the analyte sensor may be configured in a stacked, side by side or layered construction or configuration such that at least a portion of each of the conducting layers is separated by a respective insulation layer (for example, a dielectric layer).

Additionally, within the scope of the present disclosure, some or all of the electrodes of the analyte sensor may be provided on the same side of the substrate in a stacked construction as described above, or alternatively, may be provided in a co-planar manner such that each electrode is disposed on the same plane on the substrate, however, with a dielectric material or insulation material disposed between the conducting layers/electrodes. Furthermore, in still another aspect, the one or more conducting layers such as the electrodes of the sensor may be disposed on opposing sides of the substrate.

Figure 8A:
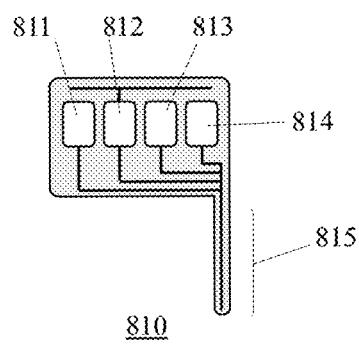
FIGS. 8A-8C illustrate a passive sensor configuration for use in a continuous analyte monitoring system, and two embodiments of an active sensor configuration for use at the patient interface in the integrated infusion device and monitoring system, respectively, in accordance with one embodiment of the present disclosure.
Figure 8C:
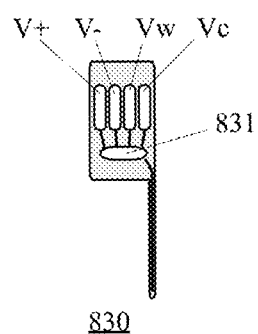
Figure 8B:
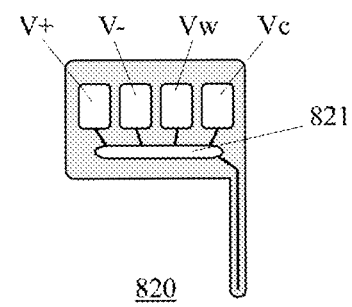

Referring again to the Figures, FIGS. 8A-8C illustrate a passive sensor configuration for use in a continuous analyte monitoring system, and two embodiments of an active sensor configuration for use at the patient interface in the integrated infusion device and monitoring system, respectively, in accordance with one embodiment of the present disclosure. Referring to FIG. 8A, analyte sensor 810 includes working electrode 811, a guard trace 812, a reference electrode 813, and a counter electrode 814. In one embodiment, the "tail" segment 815 of the analyte sensor 810 is configured to be positioned subcutaneously under the patient's skin so as to be in fluid contact with the patient.

Referring now to FIG. 8B, analyte sensor 820 is provided with the analog front end portion 821 where the four contacts shown are V+, V−, Vw, and Vc signals in accordance with one embodiment in place of the working electrode 811, a guard trace 812, a reference electrode 813, and a counter electrode 814, respectively. In this manner, in one embodiment of the present disclosure, these signals of the active analyte sensor 820 are low impedance and thus less subject to noise than the passive sensor signals. Moreover, in one embodiment, the analyte sensor 820 configuration may include a flex circuit.

Referring now to FIG. 8C, in a further embodiment, an active sensor of similar construction to the active sensor 820 of FIG. 8B but with much smaller dimensions is shown. More specifically, analyte sensor 830 is provided with four contacts configured for direct wire bonding rather than a mechanical contact system as indicated by the large contact areas on the previous two sensor configurations shown in FIGS. 8A-8B. Since the shape of the analyte sensor 830 is reduced, the sensor 830 may be wrapped around the cannula (for example, cannula 470 of FIG. 4) and thus only a single entry site may be required for the patient analyte monitoring and insulin infusion. Moreover, within the scope of the present disclosure, additional sensor/cannula configurations may be provided where the sensor circuitry and cannula are created as a single assembly such as a cannula with the circuit 831 fabricated on the surface.

Figure 9:
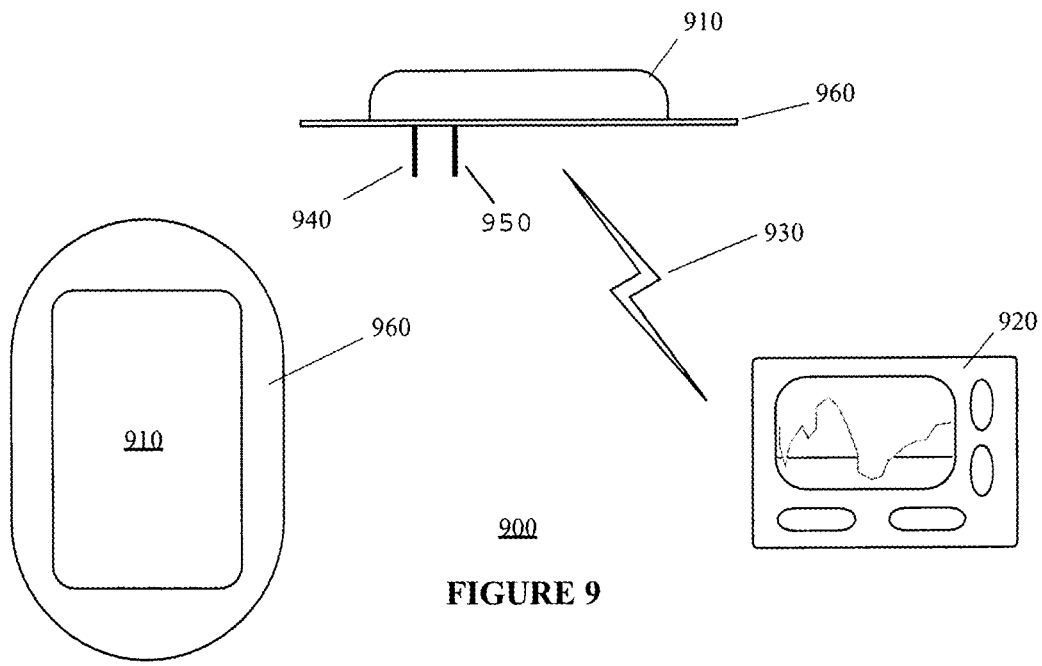
FIG. 9 illustrates an integrated infusion device and analyte monitoring system with the infusion device and the monitoring system transmitter integrated into a single patch worn by the patient in accordance with one embodiment of the present disclosure.

FIG. 9 illustrates an integrated infusion device and analyte monitoring system with the infusion device and the monitoring system transmitter integrated into a single patch worn by the patient in accordance with one embodiment of the present disclosure. Referring to FIG. 9, the integrated infusion device and analyte monitoring system 900 includes an integrated patch pump and transmitter unit 910 provided on an adhesive layer 960, and which is configured to be placed on the skin of the patient, so as to securely position cannula 950 and analyte sensor 940 subcutaneously under the skin of the patient. The housing of the integrated infusion pump and transmitter unit 910 is configured in one embodiment to include the infusion mechanism to deliver medication such as insulin to the patient via the cannula 950.

In addition, the integrated patch pump and transmitter unit 910 is configured to transmit signals associated with the detected analyte levels measured by the analyte sensor 940, over a wireless communication path 930 such as an RF link. The signals are transmitted from the on body integrated patch pump and transmitter unit 910 to a controller unit 920 which is configured to control the operation of the integrated patch pump and transmitter unit 910, as well as to receive the transmitted signals from the integrated patch pump and transmitter unit 910 which correspond to the detected analyte levels of the patient.

Referring back to FIG. 9, in one embodiment, the infusion mechanism of the integrated patch pump and transmitter unit 910 may include the infusion device of the type described in U.S. Pat. No. 6,916,159 assigned to the assignee of the present disclosure Abbott Diabetes Care Inc. In addition, while a wireless communication over the communication path 930 is shown in FIG. 9, the wireless communication path 930 may be replaced by a set of wires to provide a wired connection to the controller unit 920.

In this manner, in one embodiment of the present disclosure, the integrated infusion device and analyte monitoring system 900 does not use an infusion tubing, which may provide additional comfort and convenience to the patient by providing additional freedom from having to wear a cumbersome tubing.

Figure 10:
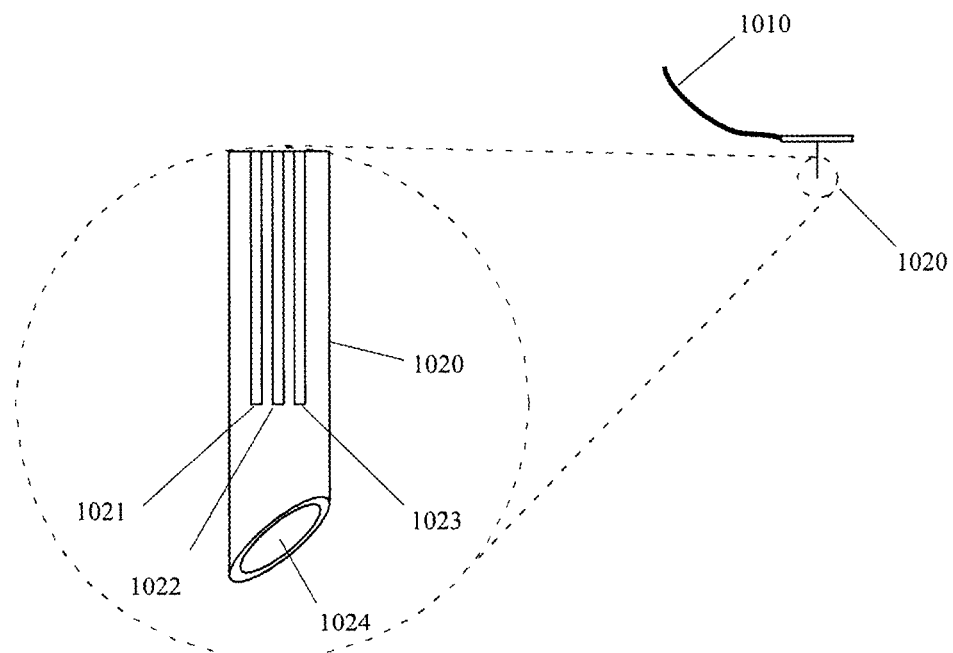
FIG. 10 is a detailed view of the infusion device cannula integrated with analyte monitoring system sensor electrodes in accordance with one embodiment of the present disclosure.

FIG. 10 is a detailed view of the infusion device cannula integrated with analyte monitoring system sensor electrodes in accordance with one embodiment of the present disclosure. Referring to FIG. 10, there is shown an infusion device cannula with analyte sensor electrodes 1020 disposed therein, and mounted to an adhesive patch 1010 so as to retain its position securely in the patient. More specifically, as can be seen from FIG. 10, the cannula with analyte sensor electrodes 1020 include sensor electrodes 1021, 1022, 1023 (which may correspond to working, reference and counter electrodes, respectively) each of which are provided within the cannula tip 1020, and further, positioned so as to maintain fluid contact with the patient's analyte. In one aspect, some or all of the electrodes of the analyte sensor may be wrapped around the cannula, stacked on one or more inner and/or outer surfaces of the cannula.

FIGS. 12A-12C each illustrate a cross sectional view of the infusion device cannula integrated with continuous analyte monitoring system sensor electrodes of FIG. 10 in accordance with the various embodiments respectively, of the present disclosure. Referring to FIG. 12A, in one embodiment, the cannula 1220 and sensor tubing 1228 are provided in parallel. More specifically, it can be seen from the Figure that cannula tubing wall 1220 provides a tube bore 1224 for insulin flow, and that each of the three insulated wires are provided with an outer casing or insulation layer 1225 of tubing wall individually surrounding each insulated wire 1221, 1222, 1223 and further, where the three insulated wires 1221, 1222, 1223 are in turn surrounded by the sensor tubing wall 1228.

Referring now to FIG. 12B in one embodiment of the present disclosure, the insulated wires 1221, 1222, 1223 respectively connected to the sensor electrodes are co-extruded into tubing wall 1220, with the tube bore 1224 for insulin delivery and the insulated wires 1221, 1222, 1223 configured substantially as shown in the FIG. 12B. Referring now to FIG. 12C, in still a further embodiment of the present disclosure, each of the insulated wires 1221, 1222, 1223 (each insulated by an insulation layer 1225) are wrapped around the tubing 1220 and covered with a sheath 1210, thus providing the tubing wall 1220, the tubing bore 1224 for insulin delivery, the individual insulated wires 1221, 1222, 1223, and the outer protective sheath 1210, which may also serve as an electromagnetic shield to eliminate electronic noise as substantially shown in the Figure.

Referring again to the Figures, the embodiments shown in FIGS. 12A and 12C may have a larger cross-sectional area (thus a larger hole needed to be punctured on the skin of the patient), but are likely easier to manufacture, more reliable and easier to make connection to the analyte sensor electronics). Additionally, within the scope of the present disclosure, an optical data transmission (i.e. fiber optics) along insulin delivery tubing between sensor and pump may be provided instead of integral wires as discussed above.

Figure 11A:
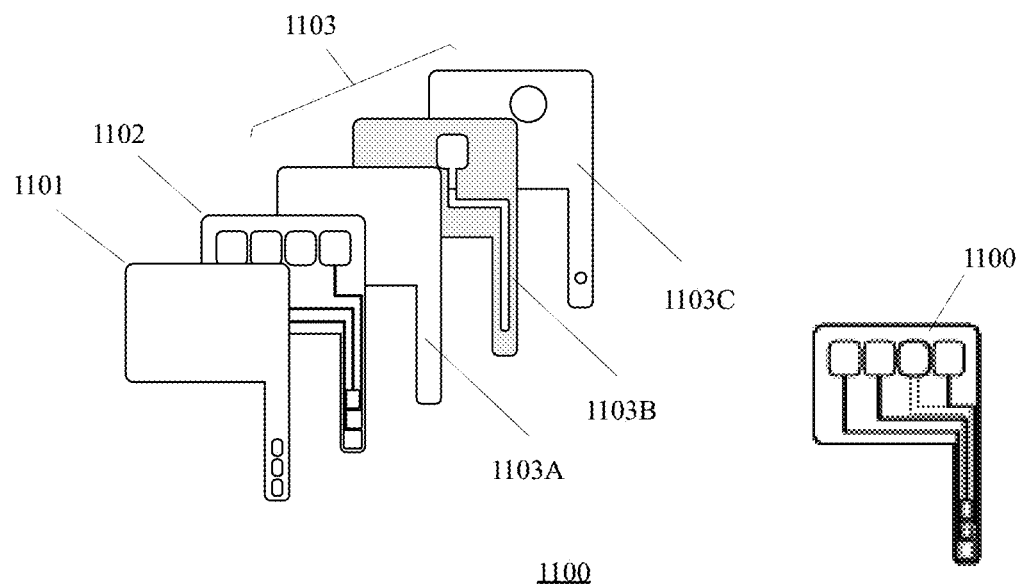
Figure 11B:
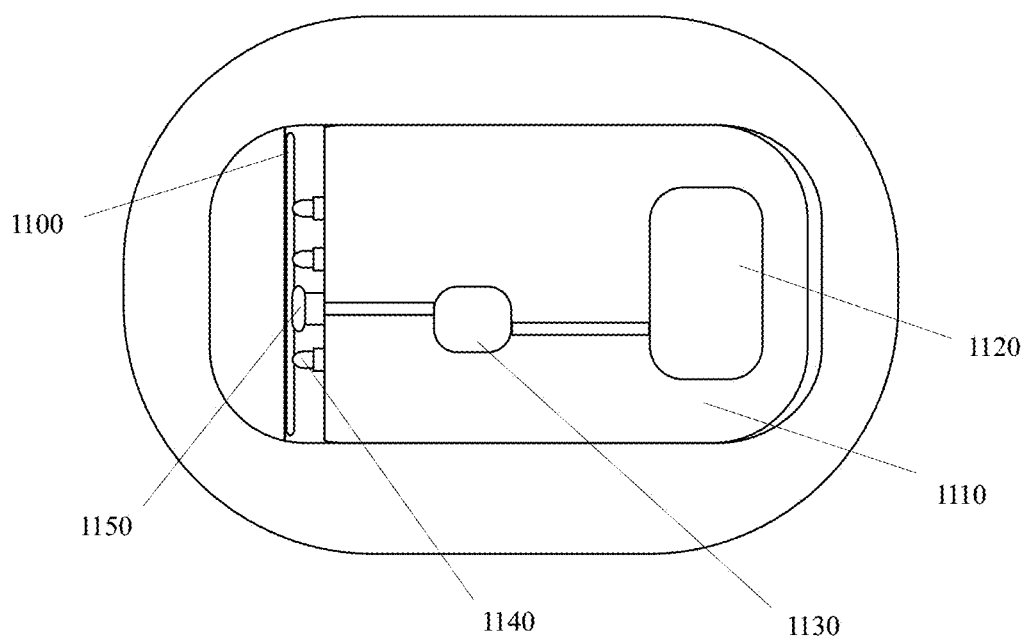
FIG. 11B illustrates a top planar view of the analyte monitoring system transmitter unit integrated with infusion device in accordance with one embodiment of the present disclosure.

FIG. 11A illustrates a component perspective view of the infusion device cannula integrated with analyte monitoring system sensor electrodes in accordance with another embodiment of the present disclosure, while FIG. 11B illustrates a top planar view of the analyte monitoring system transmitter unit integrated with infusion device in accordance with one embodiment of the present disclosure. Referring to FIGS. 11A-11B, in one embodiment of the present disclosure, integrated analyte sensor and infusion device cannula 1100 comprises five laminated layers including a top insulation layer 1101, a conductive layer 1102 with electrode traces disposed thereon, followed by three layer substrate with integrated infusion cannula 1103.

In one embodiment, the three layer substrate with integrated infusion cannula 1103 includes a separation/insulation layer 1103A to insulate the sensor electrodes from the infusion cannula, a channel layer 1103B configured to guide the flow of the insulin or any other suitable medication, and an inlet/outlet layer 1103C. Also shown in FIG. 11A is an assembled view of the integrated analyte sensor and infusion device cannula 1100.

Referring now to FIG. 11B, it can be seen that a patch pump as shown in one embodiment is provided with a transmitter unit 1110 and an insulin pump 1130 coupled to insulin reservoir 1120, and operatively coupled or mounted to the transmitter unit 1110. Also shown in FIG. 11B are the analyte sensor contacts 1140 which are configured to establish electrical contact with the respective electrodes of the integrated infusion cannula and analyte sensor 1100. Also shown in FIG. 11B is insulin port 1150 which is connected to the channel layer 1103B of the integrated infusion device cannula and analyte sensor 1100.

In this manner, in one embodiment of the present disclosure, the patch pump may be worn by the patient on skin and which includes the insulin infusion mechanism as well as the analyte sensor and transmitter unit.

FIG. 13 is a timing chart for illustrating the temporal spacing of blood glucose measurement and insulin delivery by the integrated infusion device and monitoring system in one embodiment. More specifically, insulin pumps typically deliver insulin in a periodic manner with the period of delivery in the range of 2 to 3 minutes and the duration of delivery at each period being on the order of a few seconds or less. The amount of insulin that is delivered each period may be varied depending on the overall insulin delivery rate that is desired. The analyte data is collected continuously (as, for example, a continuous current of glucose oxidation) but is typically reported to the user periodically. The analyte reporting period is typically 1 to 10 minutes and glucose oxidation current needs to be collected for 10 to 30 seconds in order to generate a reportable glucose value (to allow for filtering etc.).

Indeed, the integration of analyte monitoring and insulin delivery may necessitate placement of an analyte sensor in close proximity to an insulin infusion cannula on the body. Such close proximity engenders the possibility of insulin delivery interfering with the analyte measurements. For example, if insulin infusion should result in a localized decrease in the glucose concentration in the area of the body near the infusion site, then glucose measurement in this area would not be representative of the glucose concentration in the body as a whole. Accordingly, in one embodiment of the present disclosure, there is provided a method for temporal spacing of blood glucose measurements and insulin delivery to mitigate the possible interference between insulin infusion and glucose measurements.

In accordance with one embodiment, the temporal spacing of analyte measurement and insulin delivery may include providing a large temporal space from after insulin delivery and before taking an analyte measurement. Since both analyte measurement and insulin delivery are performed periodically, a maximum spacing in time may be achieved if analyte measurement substantially immediately precedes insulin delivery. During the time between insulin delivery and the subsequent glucose measurement, infused insulin has time to diffuse and be transported away from the infusion site due to normal circulation of interstitial fluid. An example timeline of temporally spaced analyte measurement and insulin delivery is shown in FIG. 13. If multiple analyte measurements are taken between insulin delivery points, there should always be a reading just prior to insulin delivery and as well as just after insulin delivery to minimize the effect of injected insulin on the glucose measurement readings.

Although readings are typically taken periodically for simplicity in processing, a reading may be taken out of time with other readings and scaled appropriately for the overall reading average. Similarly, the insulin delivery point may be delayed slightly until after the reading with little or no affect as the readings typically occur much more frequently than the infusions, which are intended to act over longer periods of time. In addition, other timing considerations may be considered depending on the environment in which the integrated infusion device and analyte monitoring system is used by the patient, within the scope of the present disclosure to minimize potential error on measured analyte levels and/or introduce noise or potential adverse effects to the infusion rates of the infusion device.

More specifically, fluctuation in the power supplies of the infusion device and/or the analyte monitoring system, including, for example, batteries or related power distribution circuitry, may introduce electrical noise effects, which may adversely affect the measured readings associated with the analyte monitoring system. For example, when the analyte monitoring system is configured to be in an active state so as to be transmitting or receiving data, or when the pump cycle of the infusion device is active, the power supply may be affected by the load from the data transmission/reception, or the pumping cycle. The adverse effect of the power supply in addition to noise from other components of the electronic circuitry may introduce undesirable noise and adversely affect the accuracy of the analyte sensor measurements.

Accordingly, the transmitter unit 150 (FIG. 1) for example, may be configured to monitor the timing or occurrence of the measured analyte level received from the analyte sensor 160 and the data transmission timing of the transmitter unit 150 such that the two events do not substantially overlap or occur at substantially the same time. Alternatively, the analyte monitor unit 120 (FIG. 1) may be configured to compare the timing of the analyte sensor 160 measurement and the timing of the data transmission from the transmitter unit 150, and to discard data analyte related data received from the transmitter unit 150 which coincide with the timing of the analyte measurements by the analyte sensor 160.

Moreover in one embodiment, air bubble detection in the insulin tubing may be provided, by monitoring fluid motion that would also detect the absence of fluid such as that due to an air bubble in the line. In one embodiment, the flow sensor may be configured to generate zero current when an air bubble is present.

In addition, colorization of insulin may be provided for air bubble detection in the tubing. Since pharmaceutical insulin is a clear colorless liquid, it is difficult to visually discriminate between insulin and air in tubing that carries insulin from the insulin pump to the cannula. By providing a color tint to the insulin it would be much easier to visually identify air bubbles in the tubing and be able to remove them before they cause problems. An insulin tint in one embodiment is biocompatible and insulin compatible.

In certain embodiments, the various components of the integrated system, for example, of the infusion device and analyte monitoring system 100 (FIG. 1) may need periodic replacement, where the components may require replacement at different times during the usage of the integrated system. For example, the infusion device cannula may require replacement after about each 3-days of usage, while the analyte sensor for use in the analyte monitoring system may not require replacement until at least about five or seven days of usage. Accordingly, in one embodiment, the components of the integrated system may be provided as replaceable modular components such that one or more components may be replaced at different times during the usage of the integrated system without substantially impacting the remaining portion of the integrated system.

Figure 14A:
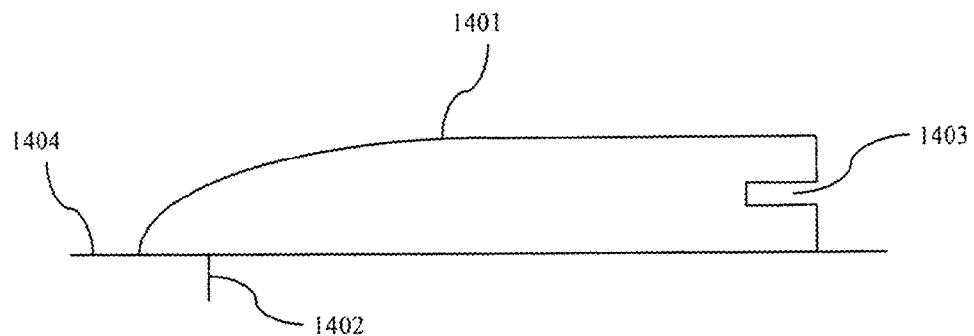
FIGS. 14A-14C illustrate modular combination of medication delivery and physiological condition monitoring system in accordance with one embodiment.
Figure 14B:
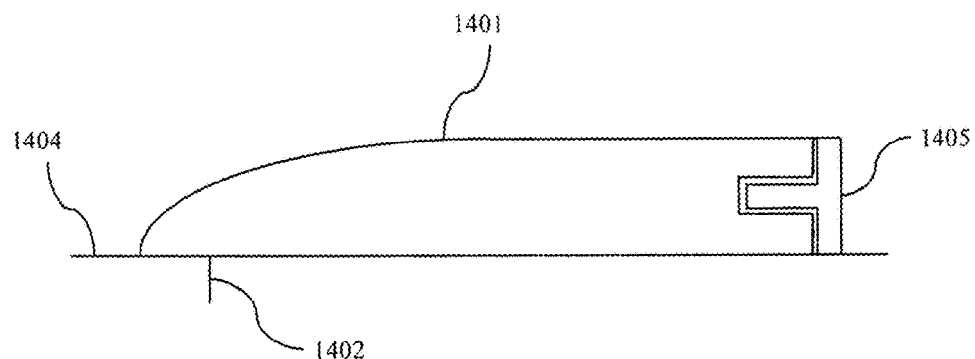
Figure 14C:
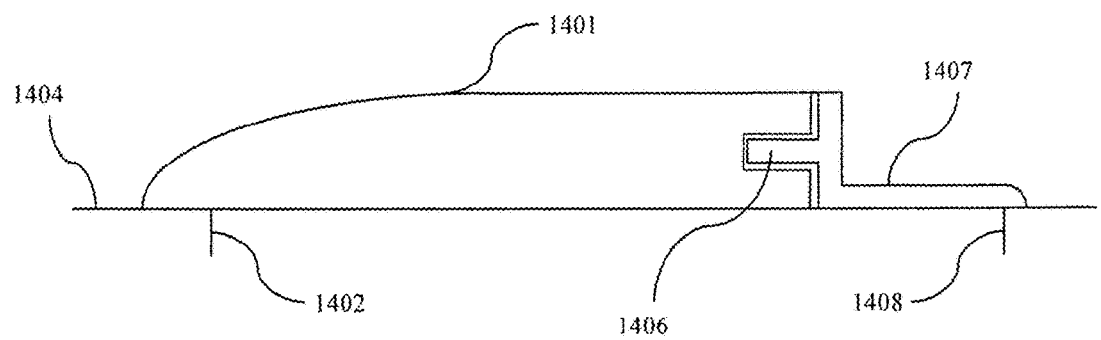

More particularly, FIGS. 14A-14C illustrate modular combination of medication delivery and physiological condition monitoring system in accordance with one embodiment. Referring to FIGS. 14A-14C, an on-body patch pump housing 1401 may be provided on the skin surface 1404 of the patient, such that the cannula 1402 is positioned transcutaneously through the patient's skin surface 1404 into the patient's body. Further shown is a connection port 1403 provided on the housing 1401 of the patch pump. As discussed in further detail below, the connection port 1403 in one embodiment may be configured to couple to an end cap 1405 (FIG. 14B) if the patch pump is used as a pump alone, or alternatively may be configured to couple to an analyte sensor connector portion 1406 when used as an integrated system with an analyte monitoring system.

Referring to the Figures, as can be seen, the analyte sensor may include a connector portion 1406, which is configured to couple to the connection port 1403 of the patch pump housing to establish a substantially water tight seal, an anchor portion 1407, which is configured to securely position the analyte sensor on the skin surface 1404 of the patient, and the tip portion 1408, which is transcutaneously positioned through the skin surface 1404 of the patient so as to be in fluid contact with the patient's analyte.

In this manner, in one embodiment, the analyte sensor may be provided as a modular component, which may be used in conjunction with the patch pump as an integrated system. Alternatively, as discussed above, the patient may select to use the patch pump alone without the continuous monitoring aspect of the integrated system. In this case, the modular system described herein may be easily used as a stand alone pump, where the end cap may be configured to provide a substantially water tight seal to the housing 1401 of the patch pump.

Alternatively, the patch pump may be used in conjunction with the analyte monitoring system wherein the patch pump housing 1401 may be configured to couple to the sensor connector portion 1406, establishing electrical contact between the sensor electrodes to the respective internal electronic components within the patch pump housing 1401. In this case, the electronic components associated with the analyte monitoring system, including the transmitter unit, processing unit and other components of analyte monitoring system may be provided substantially within the housing of the patch pump 1401.

In this manner, in certain aspects of the present disclosure, the integrated system may be used as a standalone infusion device, the patch pump and the analyte sensor may be replaced or changed independent of each other, and without substantially increasing the profile or the on-body size of the overall system, the sensor may be inserted or positioned in the patient independent of the patch pump, and also removed independent of the pump housing 1401.

Figure 15A:
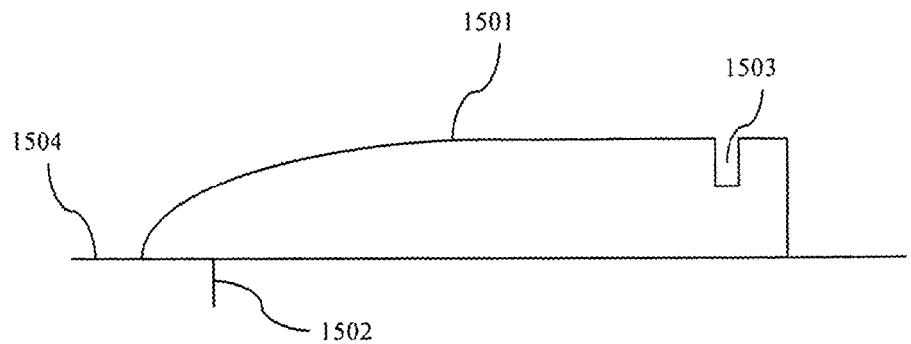
FIGS. 15A-15C illustrate modular combination of medication delivery and physiological condition monitoring system in accordance with another embodiment.
Figure 15B:
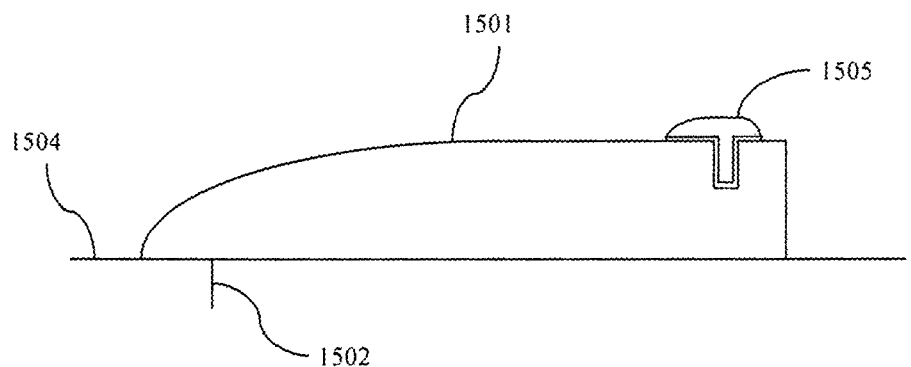
Figure 15C:
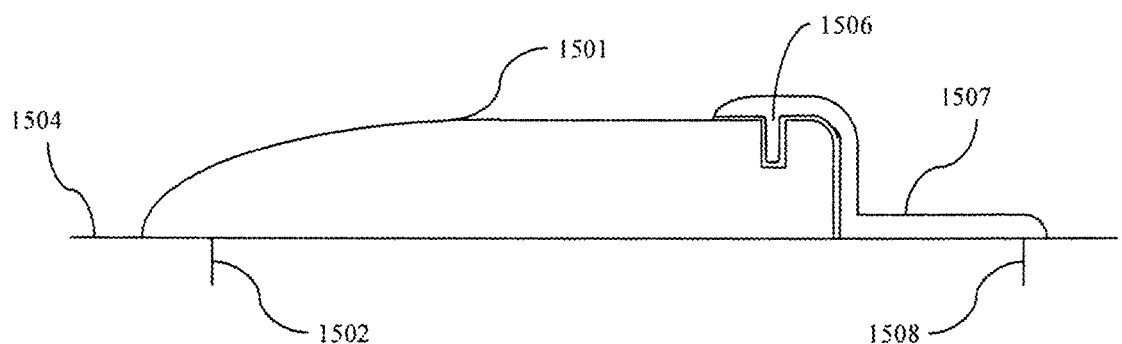

FIGS. 15A-15C illustrate modular combination of medication delivery and physiological condition monitoring system in accordance with another embodiment. Referring to the Figures, similar to the embodiment shown in FIGS. 14A-14C, the integrated system is provided with a patch pump housing 1501 which is configured for positioning on the skin surface 1504 of the patient, and which is operatively coupled to a transcutaneously positioned cannula 1502 for medication delivery to the patient.

In the embodiment shown in FIGS. 15A-15C, the connection port 1503 of the patch pump is provided substantially on the top surface of the pump housing 1501, such that, when desired, the analyte sensor connector portion 1506 may be coupled to the patch pump via the connection port 1503 from the top surface of the patch pump. Alternatively, as shown in FIG. 15B, in one aspect, a cap or a plug 1505 may be provided to seal (for example, water tight seal) the connection port 1503 when the patch pump housing 1501 is not connected to an analyte sensor, and thus for use as a stand alone infusion device. In one aspect, the cap or plug 1505 may include any suitable configuration, preferably to include a low profile physical dimension so as to maintain the low profile configuration of the on-body patch pump housing 1501.

As before, in particular embodiments, the connection port 1503 is configured to establish electrical connect with the various electrodes of the analyte sensor while providing a water tight seal at the connection. Referring again to the Figures, the analyte sensor includes an anchor portion 1507 configured to securely position the sensor on the skin surface 1504 of the patient, and a tip portion 1508 which is configured for transcutaneous placement for fluid contact with the patient's analyte.

While the embodiments described above include connection port of the patch pump housing provided on an end surface or a top surface of the pump housing, within the scope of the present disclosure, the connection port of the patch pump may be provided on any location of the patch pump housing. For example, within the scope of the present disclosure, the connection port providing a water tight seal when connected with an end cap (to establish closure), or with an analyte sensor (to use the patch pump in an integrated system with analyte monitoring), may be provided on the bottom, side, or any other surface of the patch pump housing.

Figure 16:
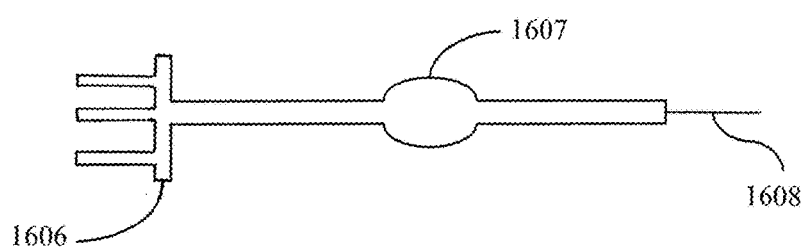
FIG. 16 illustrates a top planar view of a modular sensor component in accordance with one embodiment.

FIG. 16 illustrates a top planar view of a modular sensor component in accordance with one embodiment. More particularly, FIG. 16 illustrates the analyte sensor of FIGS. 14A-14C or 15A-15C in one embodiment. As shown, the connector portion 1606 of the analyte sensor is provided substantially on one end of the analyte sensor, while the sensing portion 1608 (for transcutaneous placement) of the analyte sensor is provided substantially on the other end of the sensor. Also shown in FIG. 16 is the anchor portion 1607, which, in one embodiment, is configured with a relatively larger width compared to other portions of the sensor.

In this manner, the anchor portion 1607 may be configured to substantially securely retain the analyte sensor on the skin surface of patient. Furthermore, one or more of the patch pump housing and the analyte sensor may be provided with an adhesive layer on the bottom surface to secure positioning on the patient's skin surface during usage. In a further aspect, the analyte sensor may comprise a flex circuit so as to provide a low profile when worn on the body of the patient.

Figure 17:
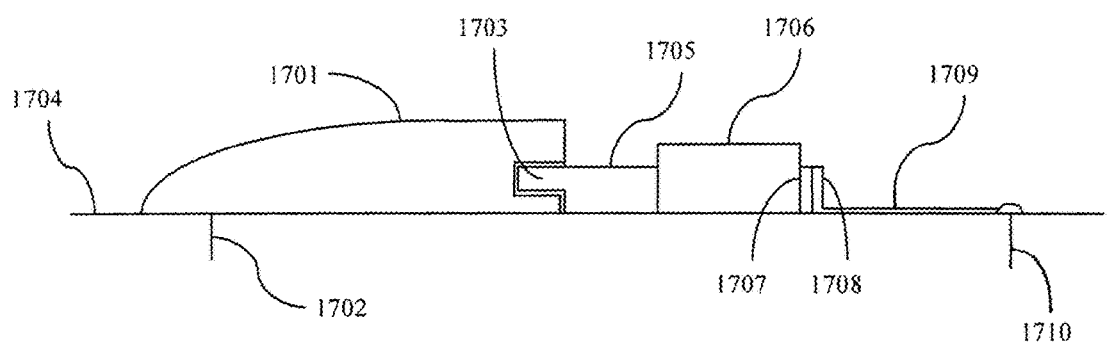
FIG. 17 illustrates modular combination of medication delivery and physiological condition monitoring system in accordance with yet another embodiment.

FIG. 17 illustrates modular combination of medication delivery and physiological condition monitoring system in accordance with yet another embodiment. Referring to FIG. 17, the patch pump 1701 is provided with a connection port 1703 and positioned on the patient's skin surface 1704 so as to securely retain the transcutaneously positioned cannula 1702 at the desired depth under the skin layer of the patient. Also shown in the Figure is a connection device 1706 which, in one embodiment, is provided with a pump connector 1705 and a sensor connector 1707. More specifically, in one embodiment, a separate modular component is provided and secured on the skin surface 1704 of the patient, and may be configured to connect to both the patch pump 1701 as well as the analyte sensor. Moreover, within the scope of the present disclosure, the connection device 1706 may be configured to further couple to other components or devices as may be desired.

Referring back to FIG. 17, in one aspect, the connection device 1706 is configured to establish electrical connection between the sensor and the patch pump such that the detected analyte levels from the tip portion 1710 of the analyte sensor is received by the suitable electronic control circuitry within the patch pump housing 1701. In an alternate embodiment, the analyte monitoring associated electronic components such as data processing units, transmitter units, and the like, may be provided within the connection device 1706. In this case, the patch pump housing 1701 may be further optimized in size.

Referring yet again to FIG. 17, the connection device 1706 is configured in one embodiment to include the pump connector 1705, which, in one embodiment, is configured to couple to the connection port 1703 of the pump to establish electrical contact and a substantially water tight seal. Furthermore, the connection device 1706 may be further configured to include a sensor connector portion 1707, which is configured to receive or connect to the connector portion 1708 of the sensor so as to establish electrical contact with the various electrodes of the sensor. That is, in one embodiment, the connector portion 1707 of the connection device 1706 may be configured to couple to the sensor connector portion 1708. Accordingly, when the sensor tip 1710 is inserted through the skin surface 1704 of the patient and in fluid contact with the patient's analytes, and retained securely in place by the adhesive tab portion 1709, the sensor connection portion 1708 is configured in one embodiment to establish electrical contact with the connection device 1706 to transfer or otherwise relay the signal level information associated with the detected analyte levels of the patient for further processing.

In this manner, in one aspect of the present disclosure, there are provided modular components or devices which comprise an integrated medication delivery and analyte monitoring system, where each component may be independently replaced, removed, or used on its own, and further, where the modular components may be used together as an integrated system for medication delivery and analyte monitoring.

Accordingly, a modular system for providing integrated medication delivery and physiological condition monitoring in one aspect includes a first modular component configured for medication delivery, and a second modular component configured to analyte level detection, where the second modular component is connectable to the first modular component to establish electrical contact with the first modular component, where a substantially water tight seal is formed when the first and second modular component are connected, and further where one of the first modular component and the second modular component is configured for replacement independent of the other component, and a third modular component connectable to the first modular component when the first modular component is disconnected with the second modular component.

In one aspect, the first modular component may include a connection port for coupling to either one of the second modular component or the third modular component.

The first modular component may include a low profile infusion device.

The second modular component may include an analyte sensor.

Further, in one aspect, a water tight seal may be formed when the first and third modular components are connected.

The first modular component in still another aspect may be configured to deliver medication to a patient at a first location in the patient, and further, wherein the second modular component is configured to detect analyte level of the patient at a second location in the patient, where the first and second locations may be separated by a predetermined distance, for example, approximately 12 inches.

The first modular component in another aspect may include a reusable portion and a disposable portion, where either of the second or third modular components is connectable to the reusable portion of the first modular component.

The disposable portion of the first modular component may include one or more of an infusion set, or a reservoir containing the medication for delivery.

The reusable portion of the first modular component may include a processing unit to control the operation of one or more of the first modular component or the second modular component.

In yet still another aspect, the system may include a communication unit disposed in one or more of the first modular component or the second modular component, the communication unit configured to transmit to or receive data from a remote location.

The remote location may include one or more of a portable control unit, a computer terminal, a server terminal, a mobile telephone, or a personal digital assistant.

The communication unit may be configured to transmit one or more signals corresponding to a respective one or more analyte levels to the remote location.

In another aspect, the communication unit may be configured to receive a flow instruction command to control delivery of the medication.

Further, in still another aspect, the communication unit may be configured to wirelessly communicate over one or more of an RF communication link, a Bluetooth® communication link, or an infrared communication link.

The second modular component in a further aspect may include an inner wall and an outer wall, a plurality of electrodes disposed between the inner wall and the outer wall, and a fluid delivery channel formed by the inner wall, where the plurality of electrodes may include an analyte sensor.

A method in accordance with another embodiment may include providing a first modular component for medication delivery, providing a second modular component configured to analyte level detection, the second modular component connectable to the first modular component to establish electrical contact with the first modular component, forming a substantially water tight seal when the first and second modular components are connected, and providing a third modular component connectable to the first modular component when the first modular component is disconnected with the second modular component, where one of the first modular component and the second modular components are configured for replacement independent of the other component.

In another aspect, the method may include delivering medication to a patient, and monitoring analyte level of the patient substantially concurrently to the medication delivery.

A modular system for providing integrated medication delivery and physiological condition monitoring in accordance with still another aspect includes a replaceable first modular component configured to deliver medication, a replaceable second modular component configured to analyte level detection, where the second modular component is connectable to the first modular component to establish electrical contact with the first modular component, and a third modular component connectable to the first modular component when the first modular component is disconnected from the second modular component, where a substantially water tight seal is formed when the first and second modular components are connected or when the first and third modular components are connected.

The one of the first modular component and the second modular components may be configured for replacement independent of the other component.

The first modular component may include a connection port to couple to either one of the second modular component or the third modular component, and further, where the third modular component may include a cap configured to couple to the connection port of the first modular component.

The cap may include an end cap or a plug.

The analyte level monitored may include glucose level.

The first modular component may include a low profile infusion device.

The second modular component may include an analyte sensor.

The first modular component may be configured to deliver medication to a patient at a first location in the patient, and further, where the second modular component may be configured to detect analyte level of the patient at a second location in the patient.

In yet a further aspect, the first and second locations are separated by a predetermined distance.

The first modular component may include a reusable portion and a disposable portion, where either of the second or third modular components are connectable to the reusable portion of the first modular component.

The disposable portion of the first modular component may include one or more of an infusion set, or a reservoir containing the medication for delivery.

The reusable portion of the first modular component may include a processing unit to control the operation of one or more of the first modular component or the second modular component.

Also the system may include a communication unit disposed in one or more of the first modular component or the second modular component, the communication unit configured to transmit to or receive data from a remote location, and further, where the remote location may include one or more of a portable control unit, a computer terminal, a server terminal, a mobile telephone, or a personal digital assistant.

The communication unit may be configured to transmit one or more signals corresponding to a respective one or more analyte levels to the remote location.

Also, the communication unit may be configured to receive a flow instruction command to control delivery of the medication.

The communication unit may be configured to wirelessly communicate over one or more of an RF communication link, a Bluetooth® communication link, or an infrared communication link.

In still yet another aspect, the second modular component may include an inner wall and an outer wall, a plurality of electrodes disposed between the inner wall and the outer wall, and a fluid delivery channel formed by the inner wall.

The plurality of electrodes may comprise an analyte sensor.

A method in accordance with another aspect includes positioning a replaceable first modular component on a skin surface of a user, connecting a replaceable second modular component to a predetermined location on the first modular component during a first time period, wherein a water tight seal is formed between the first modular component and the second modular component, and connecting a third modular component to the predetermined location first modular component during a second time period, where a water tight seal is formed between the first modular component and the second modular component, and further where the first time period and the second time period are nonoverlapping.

The method may include delivering medication to the user, and monitoring analyte level of the user.

A kit in still another aspect may include an infusion device configured to deliver medication, the infusion device including a port, an analyte monitoring device configured to monitor an analyte level of a user, the analyte monitoring device connectable to the port of the infusion device during a first predetermined time period, and a cap connectable to the port of the infusion device during a second predetermined time period, where the first and second predetermined time periods are nonoverlapping.

The infusion device may include an on-body patch pump.

The cap provides a water tight seal on the port when connected to the infusion device.

The analyte monitoring device provides a water tight seal on the port when connected to the infusion device.

In still yet a further aspect, a system including an infusion device and an analyte monitoring unit includes an infusion device, an on-body unit including a data transmission section, the on-body unit further coupled to the infusion device, the on-body unit configured to receive one or more signals corresponding to a respective one or more analyte levels, and further, the on-body unit configured to infuse a fluid received from the infusion device, and a receiver unit operatively coupled to the on-body unit, the receiver unit configured to receive data from the on-body unit, wherein the received data is associated with the analyte level.

The system may further include an analyte sensor, at least a first portion of, which is in fluid contact with an analyte of a patient, and further, where, at a second portion of, the analyte sensor is in signal communication with the data transmission section.

The data transmission section may, in one embodiment, be configured to transmit the one or more signals corresponding to a respective one or more analyte levels substantially periodically at one or more predetermined time intervals, where the one or more predetermined time intervals may include one or more of approximately 30 seconds, approximately one minute, or approximately 90 seconds.

In one aspect, the on-body unit may include a cannula, at least a portion of, which is subcutaneously positioned under a skin layer, and further, may also include an infusion tubing connected to the infusion device to deliver the fluid to the on-body unit. The infusion tubing and the on-body unit in a further aspect may be connected in a substantially water tight seal.

In yet another embodiment, the infusion tubing may be configured to operatively couple to the cannula to deliver the fluid.

The on-body unit may be configured to wirelessly transmit the one or more signals corresponding to the respective one or more analyte levels to the receiver unit, where the on-body unit and the receiver may be configured to wirelessly communicate over one or more of an RF communication link, a Bluetooth® communication link, or an infrared communication link.

In addition, the infusion device in a further embodiment may be configured to control the delivery rate of the fluid based on the one or more signals corresponding to the respective one or more analyte levels received by the receiver unit, and further, where the infusion device may be configured to determine a modified delivery protocol for delivering fluid such as insulin based on information associated with the one or more signals corresponding to the respective one or more analyte levels.

In yet another aspect, the modified delivery protocol may include one or more of a correction bolus, a modified basal profile, a carbohydrate bolus, an extended bolus, or combinations thereof.

The receiver unit in one embodiment may be configured to wirelessly communicate with the infusion device.

In a further embodiment, the receiver unit may be integrated into a housing of the infusion device.

A method of integrating analyte monitoring and fluid infusion in another embodiment of the present disclosure includes infusing a fluid at a predetermined delivery rate, detecting one or more analyte levels, transmitting one or more signals associated with the respective detected one or more analyte levels, and determining a modified delivery rate based on the transmitted one or more signals.

In one aspect, the one or more signals may be transmitted substantially immediately after the associated respective one or more analyte levels are detected.

Moreover, the transmitting step in one embodiment may include wirelessly transmitting the one or more signals which wirelessly transmitted over one or more of an RF communication link, a Bluetooth® communication link, an infrared communication link, or combinations thereof.

The method in a further aspect may also include the steps of receiving the transmitted one or more signals, and displaying the received one or more signals.

Moreover, the method may include the step of displaying the modified delivery rate. In addition, the method may also include the step of implementing the modified delivery rate, where the predetermined delivery rate may include one or more basal delivery rates.

The modified delivery rate in a further embodiment may include one or more of a correction bolus, a modified basal profile, a carbohydrate bolus, an extended bolus, or combinations thereof.

An apparatus including an analyte sensor and a fluid delivery channel in yet another embodiment of the present disclosure includes a fluid delivery unit having an inner wall and an outer wall, and a plurality of electrodes disposed between the inner wall and the outer wall of the fluid delivery unit, where a portion of the fluid delivery unit and a portion of the plurality of electrodes are subcutaneously positioned under a skin layer.

In one aspect, the plurality of electrodes may comprise an analyte sensor, including, for example, one or more of a working electrode, a counter electrode, a reference electrode, or combinations thereof.

The fluid delivery unit may include a channel for delivering a fluid such as insulin, the channel substantially formed by the inner wall.

An apparatus including an analyte sensor and a fluid delivery channel in accordance with still another embodiment of the present disclosure includes a first tubing having a first tubing channel, and a second tubing having a second tubing channel including a plurality of electrodes disposed within the second tubing channel, where at least a portion of the first tubing and at least a portion of the second tubing are subcutaneously positioned under a skin layer.

In one embodiment, the plurality of the electrodes may be substantially and entirely insulated from each other.

In another embodiment, the first tubing and the second tubing may be integrally formed such that an outer surface of the first tubing is substantially in contact with an outer surface of the second tubing.

A system including an infusion device and an analyte monitoring unit in accordance with still another embodiment of the present disclosure includes an infusion and monitoring device, an on-body unit including a data transmission section, the on-body unit further coupled to the infusion and monitoring device, the on-body unit configured to receive one or more signals corresponding to a respective one or more analyte levels, and further, the on-body unit configured to infuse a fluid received from the infusion and monitoring device, and a connector coupled at a first end to the infusion device, and further, coupled at a second end to the on-body unit, the connector configured to channel the fluid from the infusion device to the on-body unit, and further, configured to provide the one or more signals corresponding to the respective one or more analyte levels to the infusion and monitoring device.

In one aspect, the infusion and monitoring device may be configured to execute fluid delivery to a patient, and further, to detect analyte levels of the patient over a predetermined time period.

In a further aspect, the infusion and monitoring device may include a continuous glucose monitoring system.

In still another aspect, the infusion and monitoring device may include an insulin pump.

A method of fluid delivery and analyte monitoring in accordance with still another embodiment of the present disclosure includes determining a delivery profile for fluid infusion, wherein the delivery profile including a plurality of predetermined discrete fluid infusion each temporally separated by a predetermined time period, and sampling an analyte level substantially immediately prior to each predetermined discrete fluid infusion.

The method may further include the step of sampling an analyte level substantially immediately after each predetermined discrete fluid infusion.

All references cited above herein, in addition to the background and summary sections, are hereby incorporated by reference into the detailed description of the preferred embodiments as disclosing alternative embodiments and components.

Various other modifications and alternations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments.

What is claimed is:

1. A modular system for providing integrated medication delivery and analyte level monitoring, comprising:
    a replaceable first modular component configured to deliver medication, the first modular component comprising a connection port and a processing unit;
    a replaceable second modular component configured to monitor an analyte level with a sensor tip portion, wherein the second modular component is connectable to the connection port of the first modular component to establish electrical contact between the sensor tip portion and the processing unit of the first modular component such that a signal corresponding to the analyte level passes from the sensor tip portion, through the connection port, and is received at the processing unit; and
    a third modular component connectable to the connection port of the first modular component only when the second modular component is disconnected from the connection port, wherein the first modular component is operable when the third modular component is connected to the connection port of the first modular component;
    wherein a first substantially water tight seal is formed at the connection port when the first and second modular components are connected, or a second substantially water tight seal is formed at the connection port when the first and third modular components are connected,
    wherein the first modular component comprises a reusable portion and a disposable portion, the disposable portion including one or more of an infusion set or a reservoir containing the medication for delivery, and
    wherein either of the second or third modular components are connectable to the reusable portion of the first modular component.

2. A modular system for providing integrated medication delivery and analyte level monitoring, comprising:
    a replaceable first modular component configured to deliver medication, the first modular component comprising a connection port, a processing unit, and a tubular member configured to deliver medication at a first insertion site in a patient;
    a replaceable second modular component comprising a sensor tip portion configured to detect an analyte level at a second insertion site in the patient, wherein the second modular component is connectable to the connection port of the first modular component to establish electrical contact between the sensor tip portion and the processing unit of the first modular component such that a signal corresponding to the analyte level passes from the sensor tip portion, through the connection port, and is received at the processing unit; and
    a third modular component connectable to the connection port of the first modular component only when the second modular component is disconnected from the connection port, wherein the first modular component is operable when the third modular component is connected to the connection port of the first modular component;
    wherein a first substantially water tight seal is formed at the connection port when the first and second modular components are connected, or a second substantially water tight seal is formed at the connection port when the first and third modular components are connected, and
    wherein the first insertion site is associated with a first puncture and the second insertion site is associated with a second puncture different from the first puncture.

3. The system of claim 2, wherein one of the first modular component and the second modular component is configured for replacement independent of the other component.

4. The system of claim 2, wherein the third modular component includes a cap configured to couple to and directly contact the connection port of the first modular component.

5. The system of claim 2, wherein an analyte detected by the sensor tip is glucose.

6. The system of claim 2, wherein the first modular component includes a low profile medication infusion device.

7. The system of claim 2, wherein the first and second insertion sites are separated by a predetermined distance.

8. The system of claim 7, wherein the predetermined distance is less than approximately 12 inches.

9. The system of claim 2, wherein the first modular component includes a reusable portion and a disposable portion, wherein either of the second or third modular components are connectable to the reusable portion of the first modular component.

10. The system of claim 9, wherein the disposable portion of the first modular component includes one or more of an infusion set or a reservoir containing the medication for delivery.

11. The system of claim 9, wherein the processing unit is programmed to control the operation of one or more of the first modular component or the second modular component.

12. The system of claim 2, including a communication unit disposed in one or more of the first modular component or the second modular component, the communication unit configured to transmit to or receive data from a remote location.

13. The system of claim 12, wherein the remote location includes one or more of a portable control unit, a computer terminal, a server terminal, a mobile telephone, or a personal digital assistant.

14. The system of claim 12, wherein the communication unit is configured to wirelessly transmit data corresponding to the analyte level to the remote location.

15. The system of claim 12, wherein the communication unit is configured to receive a flow instruction command to control delivery of the medication.

16. The system of claim 2, wherein the connection port is located on one of a top surface or an end of the first modular component.

17. The system of claim 2, wherein the first modular component comprises a low profile configuration and the third modular component comprises a profile so as to maintain the low profile configuration of the first modular component when the third modular component is connected to the connection port of the first modular component.

18. The system of claim 17, wherein the second modular component comprises a profile so as to maintain the low profile configuration of the first modular component when the second modular component is connected to the connection port of the first modular component.

19. The system of claim 2, wherein the connection port comprises a receptacle configured for receiving a corresponding mating portion of the second modular component and a corresponding mating portion of the third modular component, wherein the two corresponding mating portions have similar configurations.

20. The system of claim 2, wherein the processing unit is within a housing of the first modular component, and wherein the first modular component includes an electronic pump controlled by the processing unit, wherein the electronic pump is also within the housing of the first modular component.

* * * * *